(12) United States Patent
Yamanishi

(10) Patent No.: US 6,847,835 B1
(45) Date of Patent: Jan. 25, 2005

(54) TRANSCUTANEOUS BILIRUBIN CONCENTRATION MEASURING APPARATUS AND A MEASUREMENT DATA CHECKING PLATE FOR USE WITH THE SAME

(75) Inventor: Akio Yamanishi, Hyogo-Ken (JP)

(73) Assignee: Minolta Co., Ltd., Osaka (JP)

( * ) Notice: Subject to any disclaimer, the term of this patent is extended or adjusted under 35 U.S.C. 154(b) by 0 days.

(21) Appl. No.: 09/536,762

(22) Filed: Mar. 28, 2000

(30) Foreign Application Priority Data

Mar. 31, 1999 (JP) .......................................... 11-092632

(51) Int. Cl.⁷ ................................................. A61B 5/00
(52) U.S. Cl. ...................... 600/315; 600/322; 600/310
(58) Field of Search ................................. 600/309–310, 600/315, 316, 322, 326, 336, 473–476; 356/39–42

(56) References Cited

U.S. PATENT DOCUMENTS

| | | | |
|---|---|---|---|
| 4,236,826 A | | 12/1980 | Yamanishi |
| 4,267,844 A | | 5/1981 | Yamanishi |
| 5,297,554 A | * | 3/1994 | Glynn et al. ................. 600/476 |
| 5,353,790 A | | 10/1994 | Jacques et al. |
| 5,513,642 A | * | 5/1996 | Ostrander ..................... 600/334 |
| 5,770,454 A | * | 6/1998 | Essenpreis et al. .......... 436/164 |
| 5,791,345 A | * | 8/1998 | Ishihara et al. .............. 600/368 |
| 5,825,488 A | * | 10/1998 | Kohl et al. .................... 356/342 |
| 5,830,132 A | * | 11/1998 | Robinson ..................... 600/310 |
| 5,879,294 A | * | 3/1999 | Anderson et al. ........... 600/310 |
| 5,983,120 A | * | 11/1999 | Groner et al. ............... 600/310 |
| 6,134,458 A | * | 10/2000 | Rosenthal ..................... 600/310 |

FOREIGN PATENT DOCUMENTS

| | | |
|---|---|---|
| JP | 2-116533 | 5/1990 |
| JP | 4-127036 | 4/1992 |
| JP | 4-332535 | 11/1992 |

OTHER PUBLICATIONS

Pages 195–202 of the Journal "Pediatrics" vol. 65, No. 2, published on Feb. 1980.
Page 275 of the Japanese Journal of Medical Electronics and Biological Engineering, vol. 36 issued on May, 1998 by Japan Soc. ME & BE.

* cited by examiner

Primary Examiner—Eric F. Winakur
Assistant Examiner—Matthew Kremer
(74) Attorney, Agent, or Firm—McDermott Will & Emery LLP

(57) ABSTRACT

Luminous fluxes from a xenon tube are introduced from one end of an optical fiber to an other end thereof and emerge therefrom. These luminous fluxes are incident of a skin of a person to be measured, and those diffused in the skin are incident on one end of an optical fiber through a first incident port and on one end of an optical fiber through a second incident port. The luminous fluxes from the one end are split by a dichroic mirror. The luminous fluxes reflected by the dichroic mirror are received by a photoelectric conversion element via a blue filter, and those having transmitted through the dichroic mirror are received by a photoelectric conversion element via a green filter. A concentration of bilirubin pigmented in fat of subcutaneous tissues can be accurately measured without being influenced by a difference in the thicknesses of epidermis and derma.

18 Claims, 17 Drawing Sheets

TRANSCUTANEOUS BILIRUBIN CONCENTRATION MEASURING APPARATUS AND A MEASUREMENT DATA CHECKING PLATE FOR USE WITH THE SAME

This application is based on patent application No. 11-92632 filed in Japan, the contents of which are hereby incorporated by references.

BACKGROUND OF THE INVENTION

This invention relates to a bilirubin concentration measuring apparatus for transcutaneously measuring a bilirubin concentration in blood from the outside of a skin and a measurement data checking plate used therewith.

Generally, icterus, particularly severe icterus of new-born babies may cause a death or, even if they can escape from a death, it may progress to nuclear icterus which causes aftereffects such as cerebral palsy. Thus, the detection of icterus in an early stage is very crucial. The degree of icterus should be precisely detected by measuring a bilirubin concentration in blood serum collected from new-born babies. However, it is difficult to collect blood from all new-born babies and to measure the bilirubin concentration or it may bet often unnecessary.

Accordingly, the icterus of a patient has been diagnosed using an icterus detector disclosed in, e.g., U.S. Pat. No. 4,267,844 without collection of blood sample. This icterus detector includes a light source for emitting a light to the skin of a human body and at least two light receiving elements for responding to light components of the reflected light in at least two wavelength ranges whose absorption coefficients by bilirubin pigmented in subcutaneous fat differ from each other. The degree or stage of icterus is measured based on the outputs of the respective light receiving elements. In this way, the degree of icterus is indirectly measured by measuring the concentration of bilirubin pigmented in subcutaneous fat instead of measuring a serum bilirubin concentration.

However, since the above icterus detector measures the degree of icterus based on the reflected light from the skin, measurement results are likely to be influenced by a difference in the thicknesses of epidermis and derma located above the subcutaneous tissues containing fat where bilirubin is pigmented (e.g., a difference in the skin maturity of the new-born baby), the skin color of a patient, i.e., a race difference. Therefore, it is difficult to constantly and accurately measure the degree of icterus.

SUMMARY OF THE INVENTION

It is an object of the present invention to provide a transcutaneous bilirubin concentration measuring apparatus and a measuring data checking plate which are free of the problems residing in the prior art.

According to an aspect of the invention, a transcutaneous bilirubin concentration measuring apparatus comprises: a light emitter for emitting a first luminous flux falling in a first wavelength range and a second luminous flux falling in a second wavelength range, their bilirubin absorption coefficients differing from each other; a light emerging port for projecting the first and second luminous fluxes onto skin of a person; a first light incident port for allowing the first and second luminous fluxes having been diffused in the skin to pass therethrough; a second light incident port for allowing the first and second luminous fluxes having been diffused in the skin to pass therethrough, the second light incident port being spaced away from the light emerging port a different distance than the first light incident port; a first electric signal generator for generating a first electric signal corresponding to an intensity of the first luminous flux passed through the first light incident port, and a second electric signal corresponding to an intensity of the second luminous flux passed through the first light incident port; a second electric signal generator for generating a third electric signal corresponding to an intensity of the first luminous flux passed through the second light incident port, and a fourth electric signal corresponding to an intensity of the second luminous flux passed through the second light incident port; and a calculator for calculating a bilirubin concentration based on the first to fourth electric signals.

According to another aspect of the invention, a transcutaneous bilirubin concentration measuring apparatus comprises: a light emitter for emitting a first luminous flux falling in a first wavelength range, a second luminous flux falling in a second wavelength range, and a third luminous flux falling in a third wavelength range, the first luminous flux being absorbable by bilirubin, the second and third being hardly absorbable by bilirubin; a light emerging port for projecting the first to third luminous fluxes onto skin of a person; a light incident port for allowing the first to third luminous fluxes having been diffused in the skin to pass therethrough; an electric signal generator for generating first to third electric signals corresponding to intensities of the first to third luminous fluxes passed through the light incident port, respectively; and a calculator for calculating a bilirubin concentration based on the first to third electric signals.

According to still another aspect of the invention, a measurement data checking plate is used with a transcutaneous bilirubin concentration measuring apparatus, and comprises: a first light diffusing layer disposed in a top part of the plate and having substantially the same absorption coefficient for both a first luminous flux falling in a first wavelength range and a second luminous flux falling in a second wavelength range which are used in the bilirubin concentration measuring apparatus; and a second light diffusing layer disposed below the first light diffusing layer and having a higher absorption coefficient of the first luminous flux than of the second luminous flux.

These and other objects, features and advantages of the present invention will become more apparent upon a reading of the following detailed description and accompanying drawings.

BRIEF DESCRIPTION OF THE DRAWINGS

FIGS. 17A to 17C show a measurement data checking plate according to another embodiment of the invention, wherein FIG. 17A is a perspective view showing an external configuration of the checking plate, FIG. 17B is a sectional view showing an internal construction of a high concentration testing section, and FIG. 17C a sectional view showing an internal construction of a low concentration testing section.

DETAILED DESCRIPTION OF THE PREFERRED EMBODIMENTS OF THE INVENTION

Figure 1A:
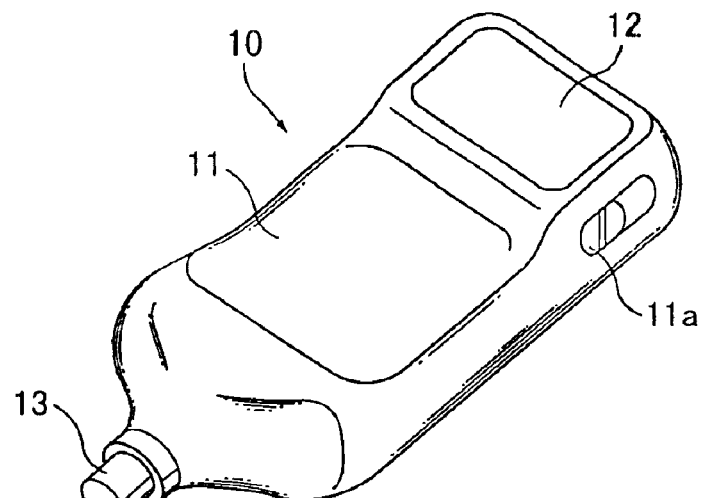
FIG. 1A is an entire perspective view showing an external configuration of a transcutaneous bilirubin concentration measuring apparatus according to a first embodiment of the invention.

A construction of a transcutaneous bilirubin concentration measuring apparatus according to a first embodiment of the invention will be described with reference to FIGS. 1A to 1C. As shown in FIG. 1A, this measuring apparatus 10 has a casing 11 of such a size holdable in hand. In this casing 11 are arranged an optical system and electric elements to be described later. Further, a display 12 for displaying a measurement result, i.e., a concentration of bilirubin pigmented in subcutaneous fat is provided at the rear end of the upper surface of the casing 11.

A cylindrical projection 13 is projectably and retractably (as indicated by an arrow AR) mountable on the leading end of the casing 11. This projection 13 is biased in such a direction as to project from the casing 11 (arrow direction AR) by a biasing means (not shown) such as a spring member. When a person who conduct a measurement presses the projection 13 against a part, such as a forehead, of a person to be measured, it is pushed into the casing 11 against a biasing force of the biasing means, thereby driving a xenon tube 21 (see FIG. 2) described later.

Figure 1B:
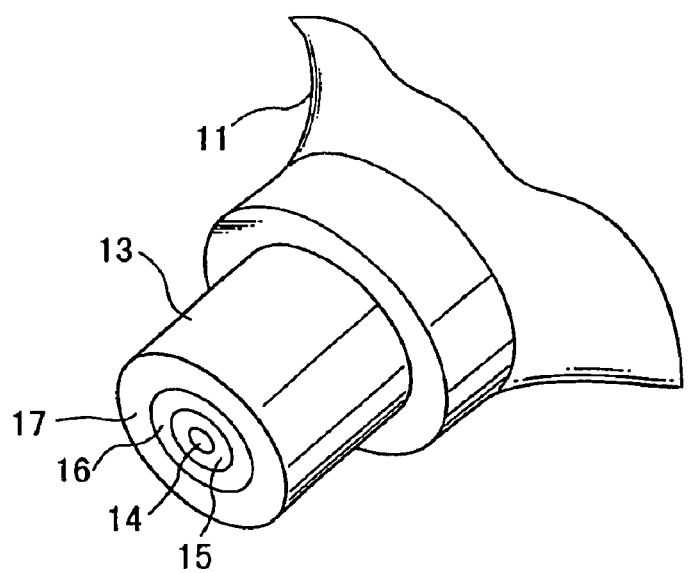
FIG. 1B is an enlarged view of an projection portion of the measuring apparatus shown in FIG. 1A.

In the middle of the end face of the projection 13 is provided, as shown in FIG. 1B, a round emerging port 14 through which luminous fluxes from the xenon tube 21 emerge out. An annular first incident port 15 is provided outside the emerging port 14, an annular second incident port 16 is provided outside the first incident port 15, and an annular light blocking portion 17 is provided at the outermost. As shown in FIG. 1C, the emerging port 14 and the first incident port 15, and the first and second incident ports 15 and 16 are partitioned by spacers 18, 19 painted in black, respectively. The light blocking portion 17 is applied with a matte finish and painted in black. Consequently, no external light is incident on the respective incident ports 15, 16.

Figure 1C:
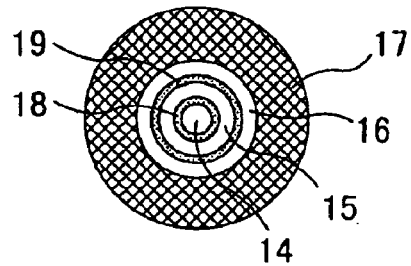
FIG. 1C is a front view of the projection portion.

When the projection 13 is pushed in to drive the xenon tube 21, white light from the xenon tube 21 emerges out through the emerging port 14 of the projection 13 shown in FIG. 1C and is incident on the skin of the person to be measured. Luminous fluxes diffused in the skin as described later are incident on the optical system provided in the casing 11 via the first and second incident ports 15, 16. Further, a power switch 11a and a reset switch 45 (see FIG. 3) are provided at a rear end of one side surface of the casing 11 in FIG. 1A and on a back surface thereof, respectively.

Figure 2:
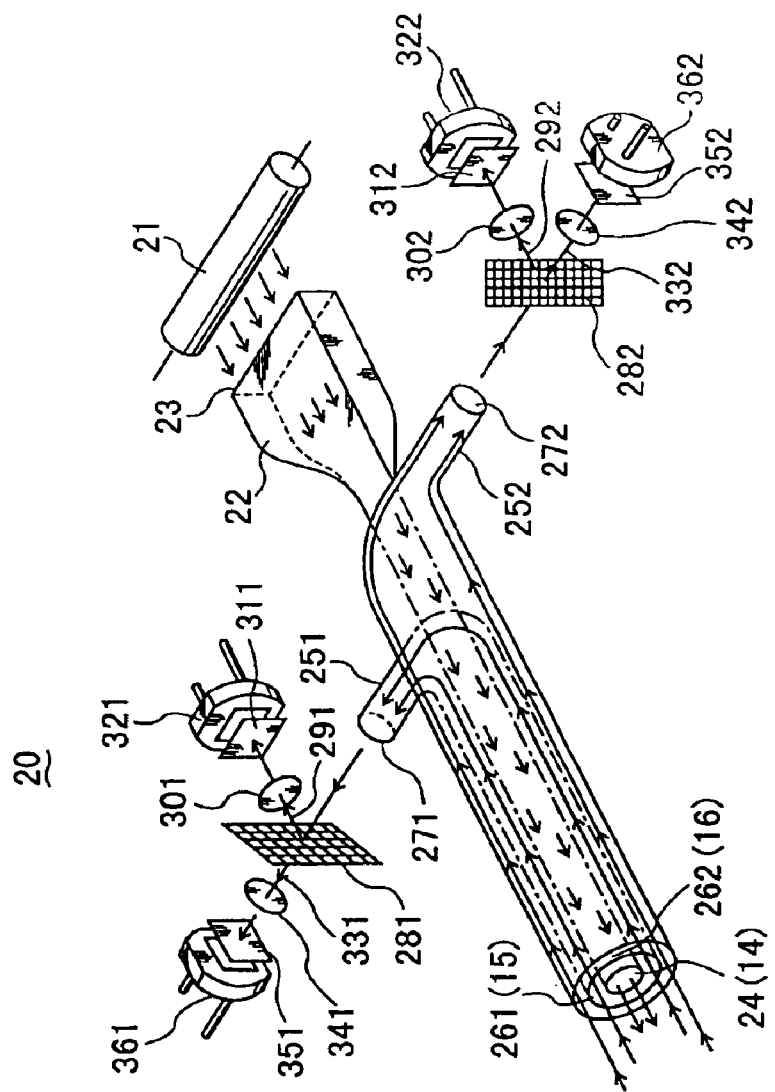
FIG. 2 is a perspective diagram showing an optical system accommodated in a casing of the measuring apparatus shown in FIG. 1A.

FIG. 2 shows an optical system 20 accommodated in the casing 11. The optical system 20 has the xenon tube 21 (light emitting means) as a light source, and a light (white light) having a plurality of wavelengths is produced when the xenon tube 21 is driven.

One end 23 of an optical fiber 22 which acts as a guiding means is opposed to the xenon tube 21. The light from the xenon tube 21 is introduced to an other end 24 of the optical fiber 22, and emerges out through the emerging port 14 of the projection 13 (see FIG. 1) therefrom. The emergent luminous fluxes are incident on the skin of the person to be measured, and those diffused in the skin as described later are incident on one end 261 of an optical fiber 251 via the first incident port 15 and on one end 262 of an optical fiber 252 via the second incident port 16 from the outer surface of the skin. In other words, the emerging port 14 coincides with the other end 24 of the optical fiber 22, the first incident port 15 coincides with the other end 261 of the optical fiber 251 and the second incident port 16 coincides with the one end 262 of the optical fiber 252.

The diffused luminous fluxes incident on the one end 261 of the optical fiber 251 are introduced to the other end 271 and emerged therefrom, whereas those incident on the one end 262 of the optical fiber 252 are introduced to the other end 272 and emerge therefrom.

The luminous fluxes emerged from the other ends 271 (272) are incident on a dichroic mirror 281 (282) for reflecting luminous fluxes in a blue wavelength range, thereby splitting them in two directions.

The luminous fluxes 291 (292) reflected by the dichroic mirror 281 (282) are gathered by a focusing lens 301 (302) and received by a photoelectric conversion device 321 (322) such as a photodiode via a blue filter 311 (312). The luminous fluxes having transmitted through the dichroic mirror 281 (282) are gathered by a focusing lens 341 (342) and received by a photoelectric conversion device 361 (362) such as a photodiode via a green filter 351 (352).

The optical fiber 251 constructs a first light guiding means, and the optical fiber 252 constructs a second light guiding means. Further, the photoelectric conversion device 321 constructs a first photoelectric conversion means; the photoelectric conversion device 361 constructs a second photoelectric conversion means; the photoelectric conversion device 322 constructs a third photoelectric conversion means; and the photoelectric conversion device 362 constructs a fourth photoelectric conversion means. Furthermore, the dichroic mirror 281 constructs a first splitting means, and the dichroic mirror 282 constructs a second splitting means.

The optical fibers 23, 251, 252 are each formed by a bundle of a multitude of fine fibers made of glass or synthetic resin.

By the optical system 20 constructed as above, the luminous fluxes in the blue wavelength range (first wavelength range) are incident on the photoelectric conversion devices 321, 322, and those in a green wavelength range (second wavelength range) are incident on the photoelectric conversion devices 361, 362. If light reception amounts of the photoelectric conversion devices 321, 322 are $I_1(\lambda b)$, $I_2(\lambda b)$, and those of the photoelectric conversion device 361, 362 are $I_1(\lambda kg)$, $I_2(\lambda g)$, the following relationships are established:

$I_1(\lambda b) < I_1(\lambda g)$, $I_2(\lambda b) < I_2(\lambda g)$ since bilirubin pigmented in the subcutaneous fat has a larger absorption coefficient (absorption factor) for luminous fluxes in the blue wavelength range.

Figure 3:
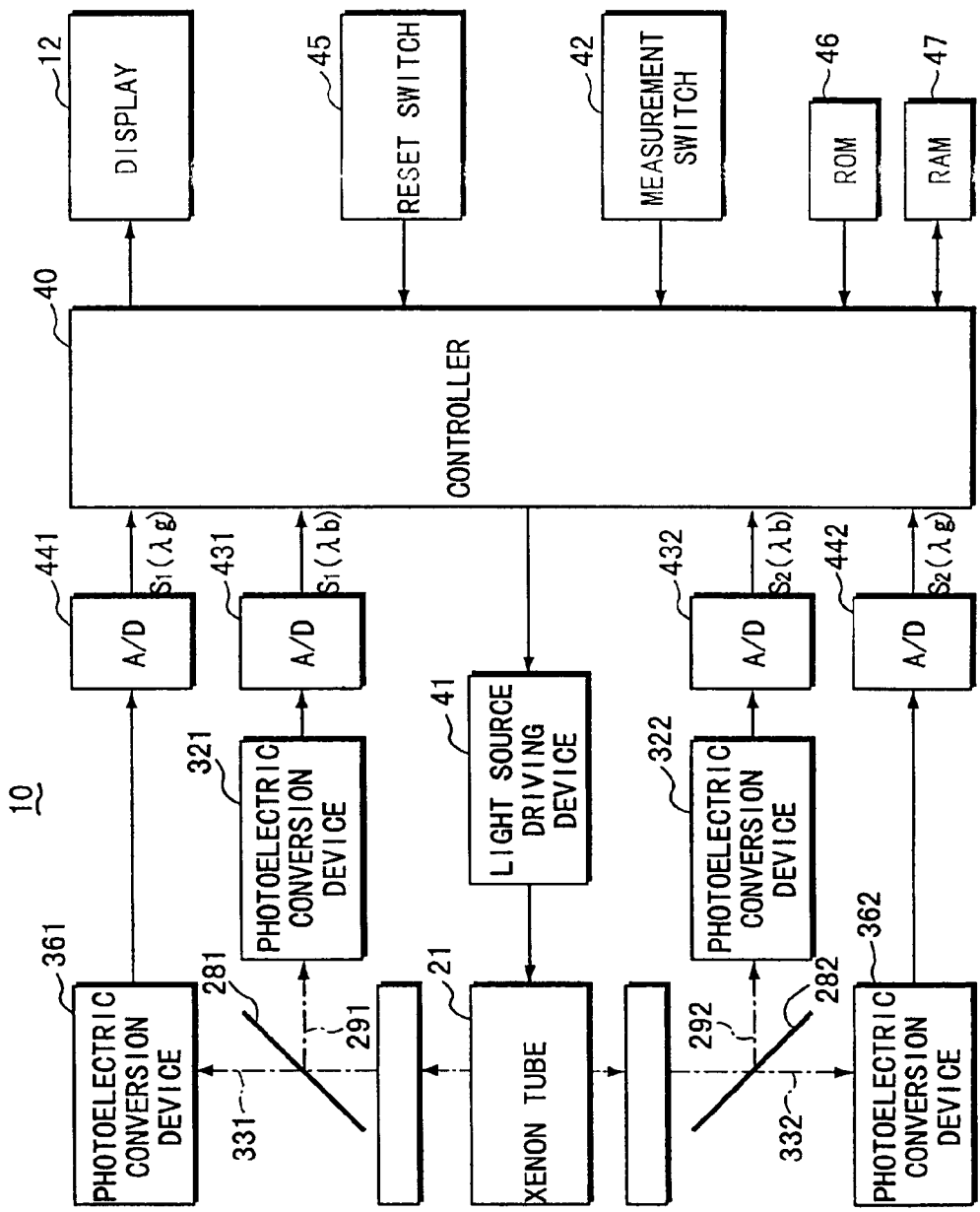
FIG. 3 is a block diagram showing an electric construction of the measuring apparatus shown in FIG. 1A.

FIG. 3 is a block diagram showing an electric construction of the bilirubin concentration measuring apparatus 10 shown in FIG. 1A. This measuring apparatus 10 is provided with a controller 40 comprised of a CPU, etc., a light source driving device 41 for driving the xenon tube 21, a measurement switch 42 which is automatically turned on when the projection 13 (see FIG. 1) is pushed into the casing 11 against the biasing force of the biasing means as described above, analog-to-digital (A/D) converters 431, 432, 441, 442, a reset switch 45 for clearing the measurement result and bringing the apparatus into a state ready for a next measurement, a ROM 46 for storing a control program for the controller 40 and fixed data set in advance, and a RAM 47 for temporarily storing electric signal data. The RAM 47 has a backup power supply (not shown) lest the content in the memory should be erased. Instead of the RAM 47 having the backup power supply, a reloadable nonvolatile memory such as an EEPROM may be used as a storage means.

The controller 40 has a function as a light emission control means and is electrically connected with the light source driving device 41. AS the projection 13 is pushed to a specified position in the casing 11 against the biasing force of the biasing means as described above, the measurement switch 42 is automatically turned on and an emission command signal is accordingly sent from the controller 40 to the light source driving device 41, which in turn drives the xenon tube 21.

The photoelectric conversion devices 321, 361 for receiving the luminous fluxes 291, 331 having transmitted through the optical fiber 251 (see FIG. 2) and having been split by the dichroic mirror 281 are electrically connected with the controller 40 via the A/D converters 431, 441, respectively. Electric signals $S_1(\lambda b)$, $S_1(\lambda g)$ proportional to the light reception amounts $I_1(\lambda b)$, $I_1(\lambda g)$ are outputted from the photoelectric conversion devices 321, 361 to the controller 40.

Likewise, the photoelectric conversion devices 322, 362 for receiving the luminous fluxes 292, 332 having transmitted through the optical fiber 252 (see FIG. 2) and having been split by the dichroic mirror 282 are electrically connected with the controller 40 via the A/D converters 432, 442, respectively. Electric signals $S_2(\lambda b)$, $S_2(\lambda g)$ proportional to the light reception amounts $I_2(\lambda b)$, $I_2(\lambda g)$ are outputted from the photoelectric conversion devices 322, 362 to the controller 40.

The controller 40 also has a function as a concentration calculating means; calculates a bilirubin concentration in accordance with a measurement principle to be described later using the electric signals $S_1(\lambda b)$, $S_1(\lambda g)$, $S_2(\lambda b)$, $S_2(\lambda g)$; and displays the calculation result on the display 12.

Figure 4:
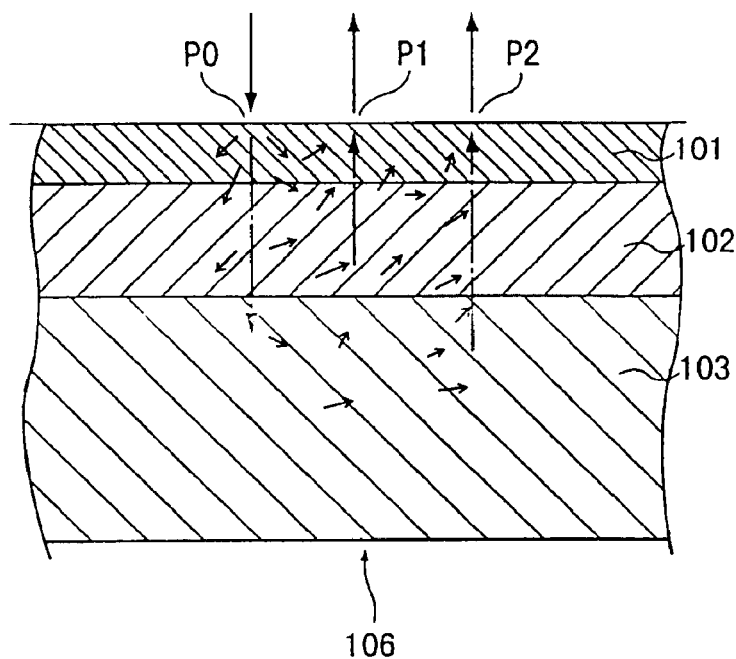
FIG. 4 is a sectional view of a new-born baby's skin diagrammatically showing optical paths when a light is incident on the skin.
Figure 5:
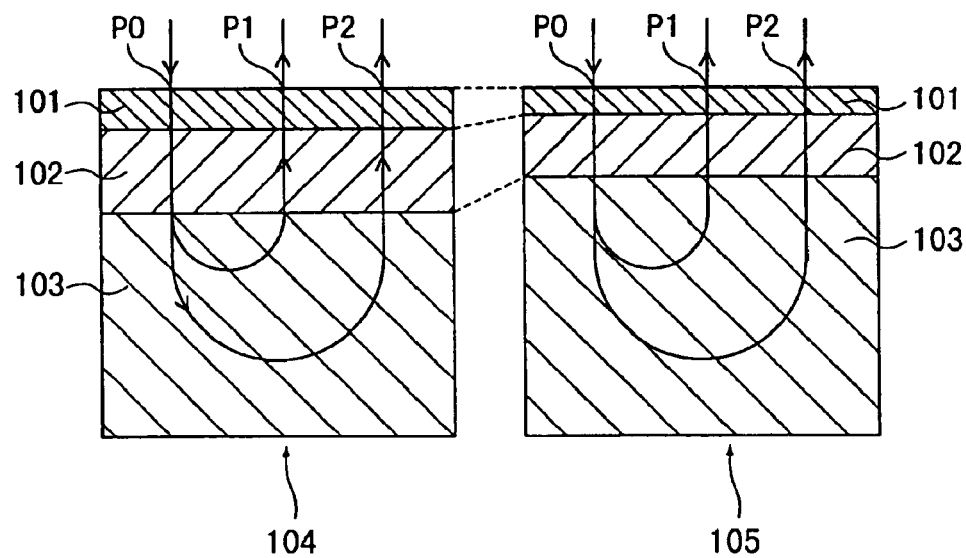
FIG. 5 is a sectional view of new-born babies' skins diagrammatically showing optical paths when a light is incident on the skins.

Next, the measurement principle of the first embodiment and the content of the calculation performed by the controller 40 are described with reference to FIGS. 4 and 5. FIGS. 4 and 5 are sectional views of new-born babies' skin diagrammatically showing optical paths when a light is incident on the skins.

As shown in FIG. 4, a human skin 106 is comprised of an epidermis 101 in which melanin is pigmented, a derma 102 in which red blood corpuscles are present, and subcutaneous tissues 103 in which bilirubin is pigmented in fat. Since the derma 102 receives only a negligible amount of blood because the outer surface of the skin 106 is pressed by the projection 13 during the measurement as described above, red blood corpuscles do not stand as a hindrance to the measurement.

In FIG. 4, it is assumed that P0 is a point of incidence of the light on the skin, and P1, P2 are points where the light from the skin emerge out, P1 being more proximate to P0 than P2. Point P0 corresponds to the emerging port 14, point P1 to the first incident port 15 and point P2 to the second incident port 16.

The luminous fluxes incident on the skin 106 at point P0 are diffused in the skin 106. A part of the luminous fluxes transmit through the epidermal 101 and the derma 102 and are incident on the measuring apparatus at points P1 and P2. On the other hand, most of the luminous fluxes having reached the subcutaneous tissues 103 are incident on the measuring apparatus at point P2 as shown in FIG. 4. Accordingly, a relationship between an average optical path length $L_1$ (hereinafter, "effective optical path length") of the luminous fluxes propagating along an optical path (hereinafter, "first optical path") extending from the point P0 of the skin 106 to the point P1 where they are incident on the measuring apparatus and an effective optical path length $L_2$ of an optical path (hereinafter, "second optical path") extending from the point P0 of the skin 106 to the point P2 where they are incident on the measuring apparatus is defined by $L_1 < L_2$ as is clear from FIG. 4.

In FIG. 5, the epidermal 101 and the derma 102 of the right skin 105 are thinner than those of a left skin 104. The left skin 104 is a standard skin, e.g., a skin of a mature baby (hereinafter, "standard skin"), whereas the right skin 105 is an undeveloped skin, e.g., a skin of a premature baby (hereinafter, "undeveloped skin").

First, the standard skin 104 on the left side of FIG. 5 is discussed. If $I_0(\lambda)$ denotes a light amount of the luminous fluxes incident on the skin 104 at point P0, a light amount $I_{1n}(\lambda)$ of the luminous fluxes incident on the measuring apparatus at point P1 is given by the following equations (1) and (2), and a light amount $I_{2n}(\lambda)$ of the luminous fluxes incident on the measuring apparatus at point P2 is given by the following equations (3) and (4) in accordance with the Lambert-Beer equation.

$$I_{1n}(\lambda) = I_0(\lambda) \cdot F_{1n} \cdot 10^{-K1n} \quad (1)$$

$$K1n = \epsilon_B(\lambda) \cdot C_B \cdot L_{1n} + \epsilon_H(\lambda) \cdot C_H \cdot L_{1n} \quad (2)$$

$$I_{2n}(\lambda) = I_0(\lambda) \cdot F_{n2} \cdot 10^{-K2n} \quad (3)$$

$$K2n = \epsilon_B(\lambda) \cdot C_B \cdot L_{2n} + \epsilon_H(\lambda) \cdot C_H \cdot L_{2n} \quad (4)$$

It should be noted that $F_{1n}$, $F_{2n}$ denote light attenuation factors on the first and second optical paths other than bilirubin and melanin, $\epsilon_B(\lambda)$ denotes an absorption coefficient of bilirubin, $C_B$ denotes a bilirubin concentration, $L_{1n}$, $L_{2n}$ denote the effective optical path lengths of the first and second optical paths, $\epsilon_H(\lambda)$ denotes an absorption coefficient of melanin, and $C_H$ denotes a melanin concentration.

Here, if it is assumed that $E_{1n}(\lambda b)$, $E_{2n}(\lambda b)$ denote measurement data obtained by the luminous fluxes in the blue wavelength range (wavelength $\lambda b$) on the first and second optical paths, the following equations (5) to (8) can be obtained from equations (1) to (4).

$$E_{1n}(\lambda b) = A_{1b} \cdot I_{1n}(\lambda b)$$
$$= A_{1b} \cdot I_0(\lambda b) \cdot F_{1n} \cdot 10^{-K1ab} \quad (5)$$

$$K1nb = \epsilon_B(\lambda b) \cdot C_B \cdot L_{1n} + \epsilon_H(\lambda b) \cdot C_H \cdot I_{1n} \quad (6)$$

$$E_{2n}(\lambda b) = A_{2b} \cdot I_{2n}(\lambda b)$$
$$= A_{2b} \cdot I_0(\lambda b) \cdot F_{2n} \cdot 10^{-K2nb} \quad (7)$$

$$K2nb = \epsilon_B(\lambda b) \cdot C_B \cdot L_{2n} + \epsilon_H(\lambda b) \cdot C_H \cdot L_{2n} \quad (8)$$

Further, let it be assumed $E_{1n}(\lambda g)$, $E_{2n}(\lambda g)$ denote measurement data obtained by the luminous fluxes in the green wavelength range (wavelength $\lambda g$) on the first and second optical paths. Since bilirubin hardly absorbs the light in the green wavelength range, it is assumed that $\epsilon_B(\lambda g) = 0$. Accordingly, the following equations (9) to (12) can be obtained from equations (1) to (4).

$$E_{1n}(\lambda b) = A_{1g} \cdot I_{1n}(\lambda g)$$
$$= A_{1g} \cdot I_0(\lambda g) \cdot F_{1n} \cdot 10^{-K1ng} \quad (9)$$

$$K1ng = \epsilon_H(\lambda g) \cdot C_H \cdot L_{1n} \quad (10)$$

$$E_{2n}(\lambda g) = A_{2g} \cdot I_{2n}(\lambda b)$$
$$= A_{2g} \cdot I_0(\lambda g) \cdot F_{2n} \cdot 10^{-K2ng} \quad (11)$$

$$K2ng = \epsilon_H(\lambda g) \cdot C_H \cdot L_{2n} \quad (12)$$

It should be noted that $A_{1b}, A_{2b}, A_{1g}, A_{2g}$ denote constants corresponding to amplification factors. These constants $A_{1b}, A_{2b}, A_{1g}, A_{2g}$ are obtained prior to an actual measurement by performing a white calibration using a white diffusing plate such as an opaque plate having no wavelength dependency as a measurement sample. Since the measurement sample is the white diffusing plate having no wavelength dependency in the white calibration, $$F_{1n} \cdot 10^{-K1nb} = F_{1n} \cdot 10^{-K1ng} = \text{constant}$$

in equations (5), (9) concerning the first optical path. Accordingly, if the constants $A_{1b}$, $A_{1g}$ are given such that $E_{1n}(\lambda b) = E_{1n}(\lambda g)$, i.e., $A_{1b} \cdot I_{1n}(\lambda b) = A_{1g} \cdot I_{1n}(\lambda g)$ in the white calibration, $$A_{1b} \cdot I_0(\lambda b) = A_{1g} \cdot I_0(\lambda g) \quad (13)$$

The thus obtained constants $A_{1b}$, $A_{1g}$ are stored in the RAM 47.

Similarly, in this white calibration, $$F_{2n} \cdot 10^{-K2nb} = F_{2n} \cdot 10^{-K2ng} = \text{constant}$$

in equations (7), (11) concerning the second optical path. Accordingly, if the constants $A_{2b}$, $A_{2g}$ are given such that $E_{2n}(\lambda b) = E_{2n}(\lambda g)$, i.e., $A_{2b} \cdot I_{2n}(\lambda b) = A_{2g} \cdot I_{2n}(\lambda g)$ in the white calibration, $$A_{2b} \cdot I_0(\lambda b) = A_{2g} \cdot I_0(\lambda g) \quad (14)$$

The thus obtained constants $A_{2b}$, $A_{2g}$ are stored in the RAM 47.

An equation: $\log\{E_{1n}(\lambda g)/E_{1n}(\lambda b)\} = K1nb - K1ng$ is obtained from equations (5), (9) concerning the first optical path and equation (13). From this equation and equations (6) and (10), the following equation (15) is obtained:

$$\log\{E_{1n}(\lambda g)/E_{1n}(\lambda b)\}$$
$$= \epsilon_B(\lambda b) \cdot C_B \cdot L_{1n} + \{\epsilon_H(\lambda b) - \epsilon_H(\lambda g)\} \cdot C_H \cdot L_{1n} \quad (15)$$

Further, an equation: $\log\{E_{2n}(\lambda g)/E_{2n}(\lambda b)\} = K2nb - K2ng$ is obtained from equations (7), (11) concerning the second optical path and equation (14). From this equation and equations (8) and (12), the following equation (16) is obtained:

$$\log\{E_{2n}(\lambda g)/E_{2n}(\lambda b)\}$$
$$= \epsilon_B(\lambda b) \cdot C_B \cdot L_{2n} + \{\epsilon_H(\lambda b) - \epsilon_H(\lambda g)\} \cdot C_H \cdot L_{2n} \quad (16)$$

From equations (15), (16), the following equation (17) is obtained:

$$\log\{E_{1n}(\lambda g)/E_{1n}(\lambda b)\} - \log\{E_{2n}(\lambda g)/E_{2n}(\lambda b)\}$$
$$= \epsilon_B(\lambda b) \cdot C_B \cdot (L_{1n} - L_{2n}) + \{\epsilon_H(\lambda b) - \epsilon_H(\lambda g)\} \cdot C_H \cdot (L_{1n} - L_{2n}) \quad (17)$$

Since a section where bilirubin is pigmented and a section where melanin is pigmented differ, the effective optical path length concerning bilirubin and the one concerning melanin differ. Accordingly, it is assumed that $L_{1nB}$, $L_{2nB}$ denote the effective optical path lengths of the first and second optical path concerning bilirubin, and $L_{1nM}$, $L_{2nM}$ denote the effective optical path lengths of the first and second optical path concerning melanin.

Since melanin is pigmented in the epidermis 101 shown in FIG. 5, the first and second optical paths are considered to have substantially equal effective optical path lengths, i.e., $L_{1nM} = L_{2nM}$ can be assumed.

Thus, the second term on the right side of equation (17) is canceled, resulting in the following equation (18):

$$\log\{E_{1n}(\lambda g)/E_{1n}(\lambda b)\} - \log\{E_{2n}(\lambda g)/E_{2n}(\lambda b)\}$$
$$= \epsilon_B(\lambda b) \cdot C_B \cdot (L_{1nB} - L_{2nB}) \quad (18)$$

equation (18) can be rewritten into:

$$C_B = J \cdot [\log\{E_{1n}(\lambda g)/E_{1n}(\lambda b)\} - \log\{E_{2n}(\lambda g)/E_{2n}(\lambda b)\}] \quad (19)$$

where $$J = 1/\epsilon_B(\lambda b) \cdot (L_{1nB} = L_{2nB}) \quad (20)$$

Now, the undeveloped skin 105 shown at the right side of FIG. 5 is discussed. Similar to the case of the aforementioned standard skin 104, if $I_0(\lambda)$ denotes a light amount of the incident luminous fluxes from point P0, a light amount $I_{1p}(\lambda)$ of the luminous fluxes incident on the measuring apparatus at point P1 is given by the following equations (21) and (22), and a light amount $I_{2p}(\lambda)$ of the luminous fluxes incident on the measuring apparatus at point P2 is given by the following equations (23) and (24).

$$I_{1p}(\lambda) = I_0(\lambda) \cdot F_{1p} \cdot 10^{-K1p} \quad (21)$$

$$K1p = \epsilon_B(\lambda) \cdot C_B \cdot L_{1p} + \epsilon_H(\lambda) \cdot C_H \cdot L_{1p} \quad (22)$$

$$I_{2p}(\lambda) = I_0(\lambda) \cdot F_{p2} \cdot 10^{-K2p} \quad (23)$$

$$K2p = \epsilon_B(\lambda) \cdot C_B \cdot L_{2p} + \epsilon_H(\lambda) \cdot C_H \cdot L_{2p} \quad (24)$$

It should be noted that $F_{1p}$, $F_{2p}$ denote light attenuation factors on the first and second optical paths other than bilirubin and melanin, $\epsilon_B(\lambda)$ denotes an absorption coefficient of bilirubin, $C_B$ denotes a bilirubin concentration, $L_{1p}$, $L_{2p}$ denote the effective optical path lengths of the first and second optical paths, $\epsilon_H(\lambda)$ denotes an absorption coefficient of melanin, and $C_H$ denotes a melanin concentration.

The undeveloped skin 105 shown at the right side of FIG. 5 has thinner epidermis 101 and derma 102 than the standard skin 104 shown at the left side. Since melanin is pigmented in the epidermis 101, the effective optical path lengths of the first and second optical paths concerning melanin in the undeveloped skin 105 are shorter than those in the standard skin 104.

However, similar to the case of the standard skin 104, the effective optical path lengths of the first and second optical paths concerning melanin are considered to be substantially equal. Thus, the effective optical path lengths $L_{1pM}$, $L_{2pM}$ of the first and second optical path concerning melanin can be assumed to be: $L_{1pM}=L_{2pM}$.

Further, as is clear from FIG. 5, the length of the optical path extending through the subcutaneous tissues 103 in the undeveloped skin 105 is longer than that in the standard skin 104. Accordingly, absolute values of the effective optical path lengths $L_{1pB}$, $L_{2pB}$ of the first and second optical paths concerning bilirubin are larger than those of the respective effective optical paths in the standard skin 104. However, a difference between the first optical path length and the second optical path length in the subcutaneous tissues 103 where bilirubin is pigmented is considered to be substantially the same regardless of the undeveloped skin 105 or the standard skin 104.

Thus, a relationship: $L_{1pB}-L_{2pB}=L_{1nB}-L_{2nB}$ is established. In other words, $(L_{1nB}-L_{2nB})$ in equation (20) is considered to be constant regardless of the thicknesses of the epidermis 101 and derma 102. Since $\epsilon_B(\lambda b)$ in equation (20) is known, it may be stored in the ROM 46. Accordingly, equation (20), i.e., J is a constant. A calibration is performed using the measurement data obtained in accordance with equation (19) by the measuring apparatus 10 and an actual measurement value of the bilirubin concentration measured according to an other method to determine the constant J. The bilirubin concentration can be precisely calculated by storing this constant J in the ROM 46 in advance.

The light reception amounts $I_1(\lambda)$, $I_2(\lambda)$ are used in equations (1) to (24) in order to facilitate the description of the measurement principle. In the controller 40 of the inventive measuring apparatus, electric signals $S_1(\lambda b)$, $S_1(\lambda g)$, $S_2(\lambda b)$, $S_2(\lambda g)$ proportional to the light reception amounts $I_1(\lambda b)$, $I_1(\lambda g)$, $I_2(\lambda b)$, $I_2(\lambda g)$ are used instead of the light reception amounts $I_1(\lambda b)$, $I_1(\lambda g)$, $I_2(\lambda b)$, $I_2(\lambda g)$ as described above. Measurement data $E_{1n}(\lambda b)$, $E_{1n}(\lambda g)$, $E_{2n}(\lambda b)$, $E_{2n}(\lambda g)$ are calculated by multiplying the electric signals by the constants $A_{1b}$, $A_{1g}$, $A_{2b}$, $A_{2g}$ corresponding to the amplification factors stored in the RAM 47. The bilirubin concentration is calculated by obtaining logarithmic values of the aforementioned quotients:

$$\log\{E_{1n}(\lambda g)/E_{1n}(\lambda b)\}$$

$$\log\{E_{2n}(\lambda g)/E_{2n}(\lambda b)\}.$$

In this case, the xenon tube 21 may be driven a plurality of times during one measurement to obtain the electric signals $S_1(\lambda b)$, $S_1(\lambda g)$, $S_2(\lambda b)$, $S_2(\lambda g)$ a plurality of times, and the measurement data $E_{1n}(\lambda b)$, $E_{1n}(\lambda g)$, $E_{2n}(\lambda b)$, $E_{2n}(\lambda g)$ may be calculated using average values of the electric signals $S_1(\lambda b)$, $S_1(\lambda g)$, $S_2(\lambda b)$, $S_2(\lambda g)$. This reduces a variation among measurements and improves the measurement accuracy.

Next, the measuring operation of the bilirubin concentration measuring apparatus 10 thus constructed is described. A person who conducts a measurement pushes the reset switch 45 after turning on the power switch 11a provided on the rear end of the side surface, thereby bringing the measuring apparatus into a measurable state. Then, the projection 13 of the measuring apparatus 10 is pressed against a part of a person to be measured, e.g., against his forehead. This causes the projection 13 to retract into the casing 11 against the biasing force of the biasing means. When the projection 13 is pushed by a specified amount, the measurement switch 42 is automatically turned on to drive the xenon tube 21, and a white light from the xenon tube 21 is projected onto the skin of the person to be measured. A part of the luminous fluxes diffused in the skin of the person to be measured are incident through the first incident port 15 and split into luminous fluxes of two colors by the dichroic mirror 281 while an other part thereof are incident through the second incident port 16 and split into luminous fluxes of two colors by the dichroic mirror 282. The luminous fluxes of the respective two colors are received by the photoelectric conversion devices 321, 361, 322, 362, which then output the electric signals $S_1(\lambda b)$, $S_1(\lambda g)$, $S_2(\lambda b)$, $S_2(\lambda g)$ proportional to the light reception amounts to the controller 40. The concentration of bilirubin pigmented in the fat of the subcutaneous tissues 103 is obtained using these electric signals, and the measurement result is displayed on the display 12.

As described above, according to the first embodiment, the first and second incident ports 15, 16 differently distanced from the emerging port 14 are provided, and the bilirubin concentration is calculated using the amounts of the luminous fluxes having transmitted along the first and second optical paths having different lengths. Accordingly, the concentration of bilirubin pigmented in the fat of the subcutaneous tissues 103 can be accurately measured without being influenced by the thicknesses of the epidermis 101 and the derma 102, i.e., the degree of maturity of the skin and also without being influenced by the melanin concentration. Therefore, the bilirubin concentration can be accurately measured regardless of whether a new-born baby is mature or premature or regardless of his race.

Further, since the light having components in the first and second wavelength ranges are emitted by the xenon tube 21, the light of a plurality of wavelengths can be emitted during one light emission, which contributes to shortening of a measurement time.

Furthermore, since the measurement switch 42 is automatically turned on to drive the xenon tube 21 when the projection 13 is pushed by the specified amount, the blood or red blood corpuscles can be eliminated from the derma constantly at a specific pressure. This enables an accurate measurement without requiring a skill.

Further, as shown in FIG. 1C, the spacer 18 is provided between the emerging port 14 and the first incident port 15, and the spacer 19 is provided between the first incident port 15 and the second incident port 16. Thus, the distance between the emerging port 14 and the first incident port 15 and that between the first incident port 15 and the second incident port 16 can be determined only by the thicknesses of the spacers 18, 19. Therefore, the respective distances can be easily controlled in the manufacturing.

Further, since the annular first incident port 15 is provided outside the round emerging port 14 and the annular second incident port 16 is provided outside the first incident port 15, an incident area of the second incident port 16 distant from the emerging port 14 can be easily increased because the radius of the second incident port 16 is larger. This makes it easier to balance the amount of light incident on the first incident port 15 and that incident on the second incident port 16.

As shown in FIG. 1B, the round emerging port 14 through which the light from the xenon tube 21 (see FIG. 2) emerges out is provided in the middle of the end face of the projection 13, the annular first incident port 15 is provided outside the emerging port 14, the annular second incident port 16 is provided outside the first incident port 15, and the annular light blocking portion 17 is provided at the outermost. As shown in FIG. 1C, the emerging port 14 and the first incident port 15, and the first incident port 15 and the second incident port 16 are partitioned by the spacers 18, 19, respectively, and the light blocking portion 17 is applied with a matte finish, painted in black so that no external light should be incident on the respective incident ports 15, 16.

The first embodiment may be modified as in following modifications (1) to (3).

Figure 6:
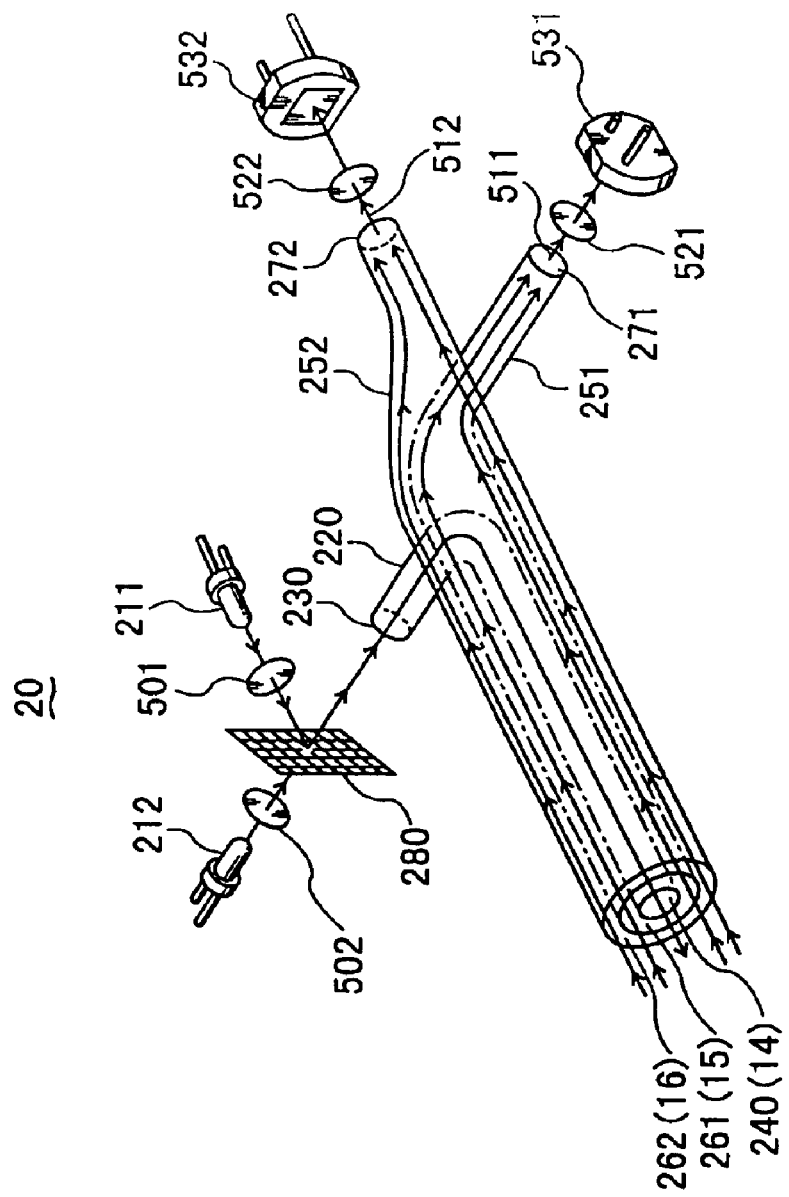
FIG. 6 is a perspective diagram showing a modification of the optical system.

(1) FIG. 6 shows a modification of the optical system 20. It should be noted that repetitive description is avoided by identifying the same members as those in FIG. 2 by the same reference numerals.

The optical system 20 of FIG. 6 is provided, as a light emission means, with a blue LED 211 for outputting luminous fluxes in the blue wavelength range (first wavelength range) and a green LED 212 for outputting luminous fluxes in the green wavelength range (second wavelength range) instead of the xenon tube 21.

The luminous fluxes emitted from the blue LED 211 are collimated by a collimator lens 501, incident on and reflected by a dichroic mirror 280 for reflecting the light components in the blue wavelength range, whereas the luminous fluxes emitted from the green LED 212 are collimated by a collimator lens 502, are incident on and transmit through the dichroic mirror 280.

One end 230 of an optical fiber 220 is opposed to the dichroic mirror 280, and the luminous fluxes having been reflected by and transmitted through the dichroic mirror 280 are incident on the one end 230 of the optical fiber 220 and introduced to an other end 240 thereof, and emerge out through the emerging port 14 (see FIG. 1) of the projection 13 therefrom.

The emerged luminous fluxes are incident on the skin of the person to be measured, and the luminous fluxes diffused in the skin are incident on one end 261 of an optical fiber 251 through the first incident port 15 from the outer surface of the, skin and also on one end 262 of an optical fiber 252 through the second incident port 16.

The diffused luminous fluxes incident on the one end 261 of the optical fiber 251 are introduced to another end 271 thereof, and emerge therefrom. On the other hand, the diffused luminous fluxes incident on the one end 262 of the optical fiber 252 are introduced to another end 272 and emerge therefrom.

The luminous fluxes 511 (512) emerged from the other end 271 (272) are gathered by a focusing lens 521 (522) and received by a photoelectric conversion device 531.

The blue LED 211 constructs a first light source, and the green LED 212 constructs a second light source. The optical fiber 251 constructs a first light guiding means, and the optical fiber 252 constructs a second light guiding means. Further, the photoelectric conversion device 531 constructs a first photoelectric conversion device, and the photoelectric conversion device 532 constructs a second photoelectric conversion device.

In the optical system 20 thus constructed, the luminous fluxes incident through the first incident port 15 are received by the photoelectric conversion device 531, whereas those incident through the second incident port 16 are received by photoelectric conversion device 532.

Figure 7:
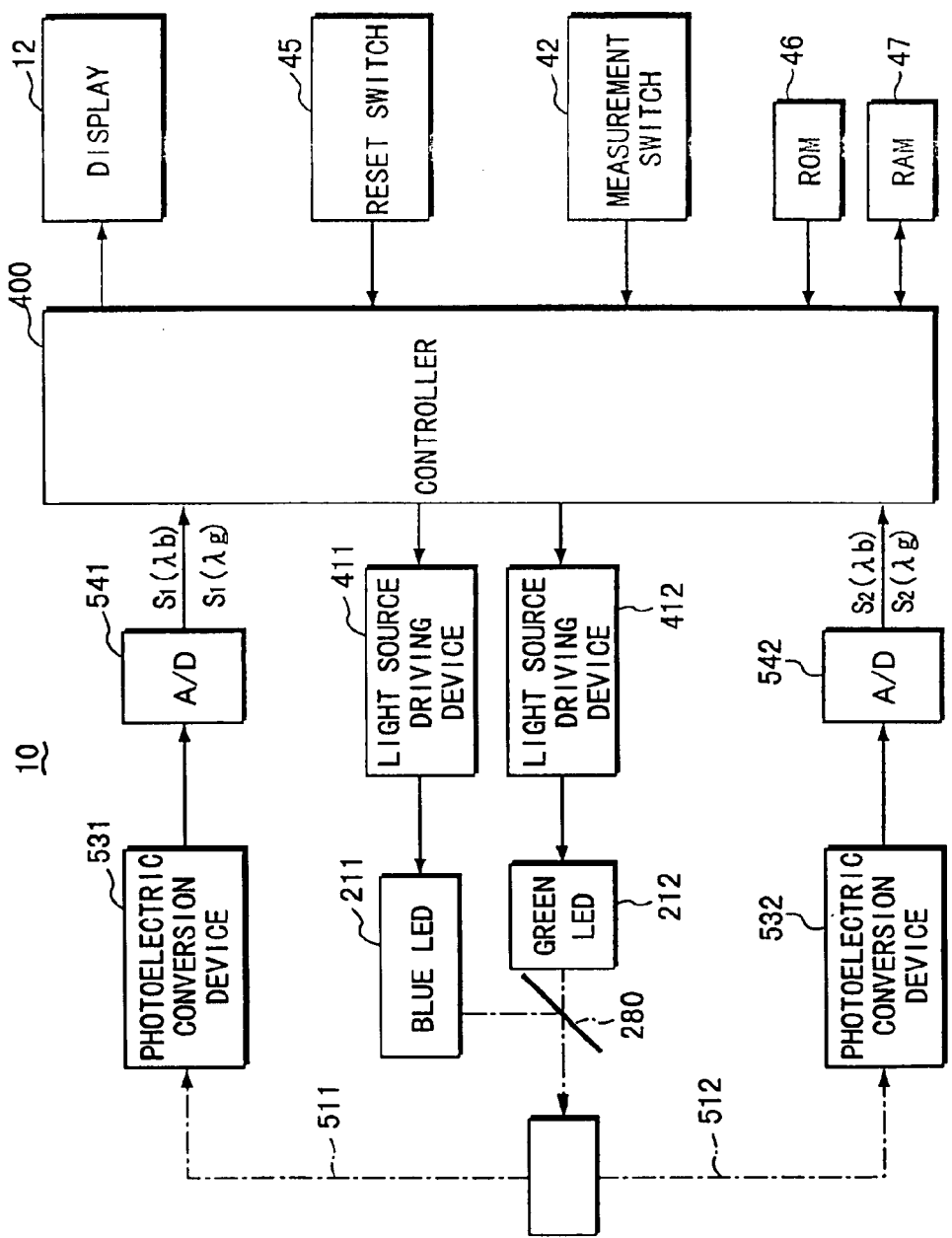
FIG. 7 is a block diagram showing an electric construction of a transcutaneous bilirubin concentration measuring apparatus having the optical system shown in FIG. 6.

FIG. 7 is a block diagram showing an electric construction of a bilirubin concentration measuring apparatus 10 having the optical system 20 shown in FIG. 6. This measuring apparatus 10 is provided with a controller 400 comprised of, e.g., a CPU, a first light source driving device 411 for driving the blue LED 211, a second light source driving device 412 for driving the green LED 212, and A/D converters 541, 542.

The controller 400 has a function as a light emission control means and are electrically connected with the first and second light source driving devices 411, 412. When the projection 13 is pushed into the casing 11 against the biasing force of the basing means, the measurement switch 42 is automatically turned on, whereupon emission command signals are individually sent from the controller 400 to the first and second light source driving means 411, 412, which in turn drive the blue LED 211 and the green LED 412, respectively.

The photoelectric conversion device 531 for receiving the luminous fluxes 511 having transmitted through the optical fiber 251 (see FIG. 2) is electrically connected with the controller 400 via the A/D converter 541. Electric signal $S_1(\lambda b)$, $S_1(\lambda g)$ proportional to light reception amounts $I_2(\lambda b)$, $I_1(\lambda g)$ are outputted from the A/D converter 541 to the controller 400. The photoelectric conversion device 532 for receiving the luminous fluxes 512 having transmitted through the optical fiber 252 (see FIG. 2) is electrically connected with the controller 400 via the A/D converter 542. Electric signals $S_2(\lambda b)$, $S_2(\lambda g)$ proportional to light reception amounts $I_2(\lambda b)$, $I_2(\lambda g)$ are outputted from the photoelectric conversion device 532 to the controller 400.

In similar to the controller 40, the controller 400 also has a function as a concentration calculating means, and calculates a bilirubin concentration in accordance with the aforementioned measurement principle using the electric signals $S_1(\lambda b)$, $S_1(\lambda g)$, $S_2(\lambda b)$, $S_2(\lambda g)$, and displays the calculation result on the display 12.

Next, a measuring operation of the measuring apparatus 10 having the optical system 20 shown in FIG. 6 is described with reference to a flowchart of FIG. 8. When a person who conducts a measurement turns on the power switch 11*a* provided on the rear end of the side surface (Step #110) and pushes the reset switch 45 (Step #120), the measuring apparatus is brought into a measurable state. Then, the projection 13 of the measuring apparatus 10 is pressed against a part of a person to be measured, e.g., against his forehead, thereby being retracted into the casing 11 against the biasing force of the biasing means (Step #130). The projection 13 is pushed (Step #130) until the measurement switch 42 is turned on (NO in Step #140).

When the projection 13 is pushed by a specified amount to turn the measurement switch 42 on (YES in Step #140), the blue LED 211 is first driven (Step #150) to project the luminous fluxes in the blue wavelength range onto the skin of a person to be measured. The luminous fluxes diffused in the skin of the person to be measured are incident through the first incident port 15 and through the second incident port 16.

The luminous fluxes incident through the first incident port 15 are received by the photoelectric conversion device 531, which in turn outputs the electric signal $S_1(\lambda b)$ proportional to the light reception amount to the controller 400. The luminous fluxes incident through the second incident port 16 are received by the photoelectric conversion device 532, which in turn outputs the electric signal $S_2(\lambda b)$ proportional to the light reception amount to the controller 400. These signals are stored in the RAM 47 (Step #160).

Subsequently, the green LED 212 is driven (Step #170) to project the luminous fluxes in the green wavelength range onto the skin of the person to be measured. The luminous fluxes diffused in the skin of this person are incident through the first incident port 15 and the second incident port 16.

The luminous fluxes incident through the first incident port 15 are received by the photoelectric conversion device 531, which in turn outputs the electric signal $S_1(\lambda g)$ proportional to the light reception amount to the controller 400. The luminous fluxes incident through the second incident port 16 are received by the photoelectric conversion device 532, which in turn outputs the electric signal $S_2(\lambda g)$ proportional to the light reception amount to the controller 400. These signals are stored in the RAM 47 (Step #180).

It is then discriminated whether the respective LEDs 211, 212 have been driven a predetermined number of times (Step #190). If they have not yet been driven the predetermined number of times (NO in Step #190), this routine returns to Step #150 to repeat the above operations.

On the other hand, if the respective LEDs 211, 211 have been driven the predetermined number of times (YES in Step #190), the bilirubin concentration is calculated in accordance with the aforementioned measurement principle using the average values of the predetermined number of data obtained (Step #200) and the measurement result is displayed on the display 12 (Step #210).

According to this modification, as shown in FIG. 6, the blue LED 211 for emitting the luminous fluxes in the first wavelength range and the green LED 212 for emitting the luminous fluxes in the second wavelength range are provided and are individually driven. Thus, the number of parts including the dichroic mirrors and the photoelectric conversion devices can be reduced as compared with the case where the optical system 20 shown in FIG. 2 is used, thereby simplifying the construction of the optical system 20. Therefore, the casing 11 can be made even smaller.

Further, the respective LEDs 211, 212, the collimator lenses 501, 502, the dichroic mirrors 280 are arranged on the same optic axis so that the luminous fluxes from the respective LEDs 211, 212 are incident on the optical fiber 220 after being collimated into parallel luminous fluxes. Therefore, the emerging angle characteristics of the luminous fluxes of the respective colors at the emerging port 14 can be in agreement with each other, with the result that measurement accuracy can be improved.

Figure 9A:
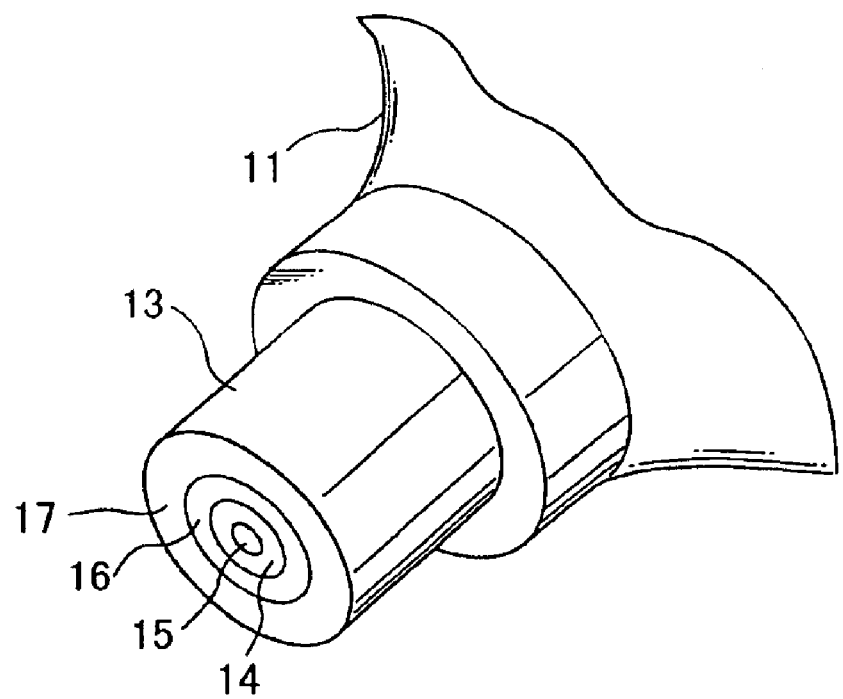
FIG. 9A is a perspective view of a modification of the projection portion.
Figure 9B:
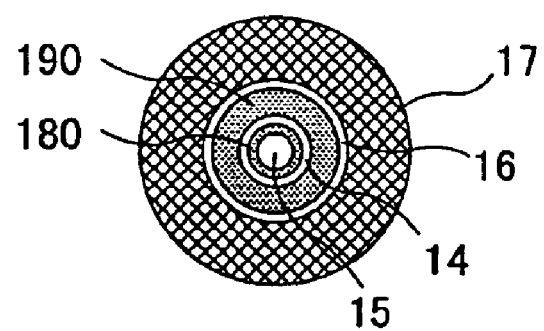
FIG. 9B is a front view of the modified projection portion.
Figure 10:
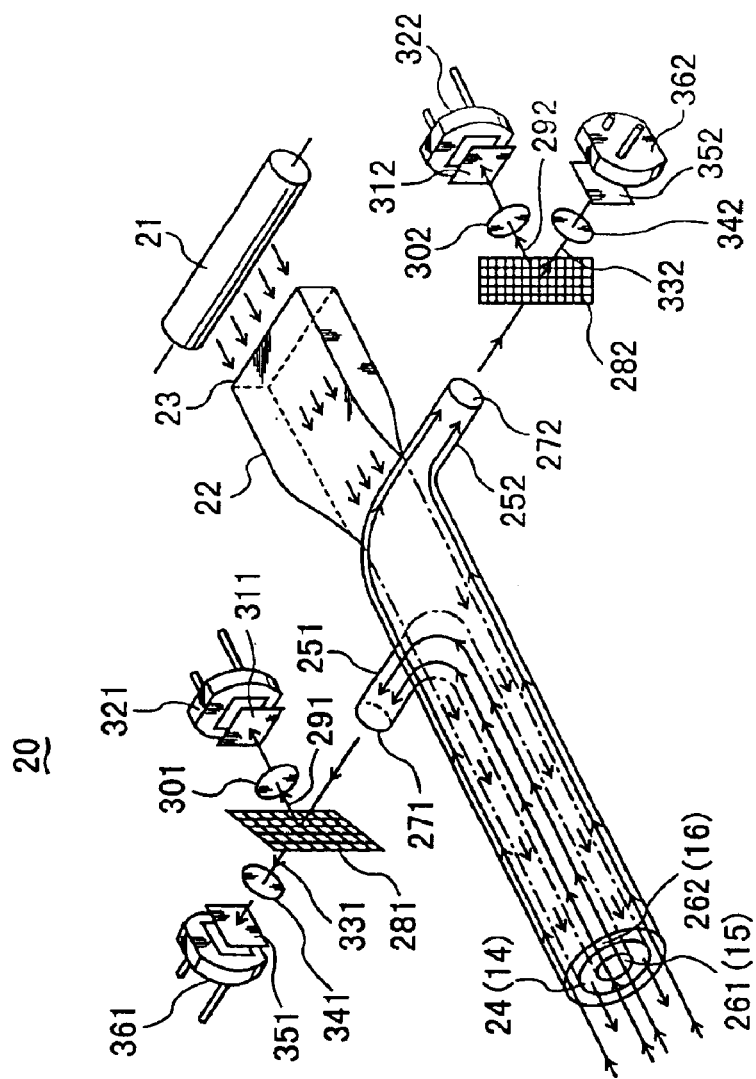
FIG. 10 is a perspective diagram showing an optical system accommodated in a casing having the projection portion shown in FIGS. 9A and 9B.

(2) FIGS. 9A and 9B are a perspective view and a front view showing a modification of the projection 13, and FIG. 10 is a diagram showing the optical system 20 accommodated in the casing 11 having the projection 13 shown in FIG. 9. It should be noted that no repetitive description is given here by identifying the same elements as those of FIGS. 1 and 2 by the same reference numerals.

In this modification, in the end face of the projection 13, a round first incident port 15 is provided in the middle, an annular emerging port 14 through which luminous fluxes from a xenon tube 21 (see FIG. 10) emerge out is provided outside the first incident port 15, an annular second incident port 16 is provided outside the emerging port 14, and an annular light blocking portion 17 is provided at the outermost as shown in FIG. 9A. Spacers 180, 190 painted in black partition the first incident port 15 and the emerging port 14, and the emerging port 14 and the second incident port 16, respectively, as shown in FIG. 9B.

This modification differs from the first embodiment in that the positions of the emerging port 14 and the first incident port 15 are switched to each other. Accordingly, one end 261 of an optical fiber 251 is round and located in the middle, and an other end 24 of the optical fiber 22 is annular and located outside the one end 261.

Generally, a distance between the emerging port 14 and the second incident port 16 needs to be set shorter than a specified value in order for the luminous fluxes to pass through an area of the subcutaneous tissues 103 of the new-born baby's skin 106 of FIG. 4 where the fat in which bilirubin is pigmented is present. In such a case, if the first incident port 15 is provided between the emerging port 14 and the second incident port 16 as in the first embodiment, the width of the first incident port 15 needs to be set smaller than a specified dimension, making the area of the first incident port 15 smaller, which may cause an insufficient amount of the incident luminous fluxes.

However, according to this modification, the distance between the emerging port 14 and the second incident port 16 is independent of the width of the first incident port 15 and the respective distances from the emerging port 14 to the first and second incident ports 15, 16 can be set only by the thickness of the spacers 180, 190. Thus, the respective distances can be easily set and a sufficient amount of the luminous fluxes through the first incident port can be ensured.

(3) The green filters 351, 352 may be replaced by red filters in the first embodiment. Alternatively, the green LED 212 may be replaced by a red LED in the modification (1). Since bilirubin does not absorb the luminous fluxes in the red wavelength range even if the luminous fluxes in the red wavelength range are used as those in the second wavelength range, the bilirubin concentration can be securely measured similar to the aforementioned cases.

Next, a transcutaneous bilirubin concentration measuring apparatus according to a second embodiment of the invention is described. Unlike the first embodiment in which the luminous fluxes in the two wavelength ranges are caused to propagate along the two optical paths in the skin, luminous fluxes in three wavelength ranges are caused to propagate along the same optical path in the skin in the second embodiment.

Figure 11A:
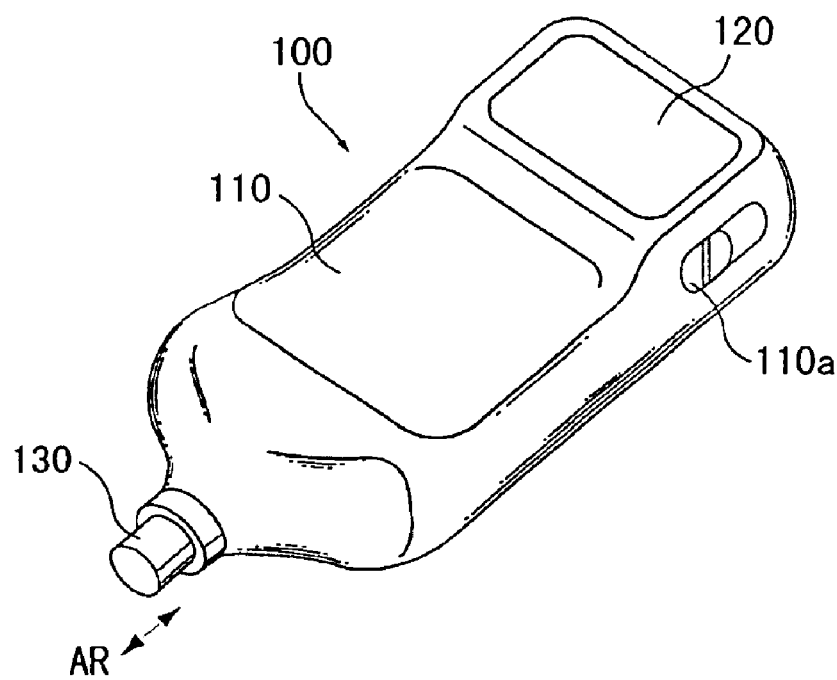
FIG. 11A is an entire perspective view showing a transcutaneous bilirubin concentration measuring apparatus according to a second embodiment of the invention.
Figure 11B:
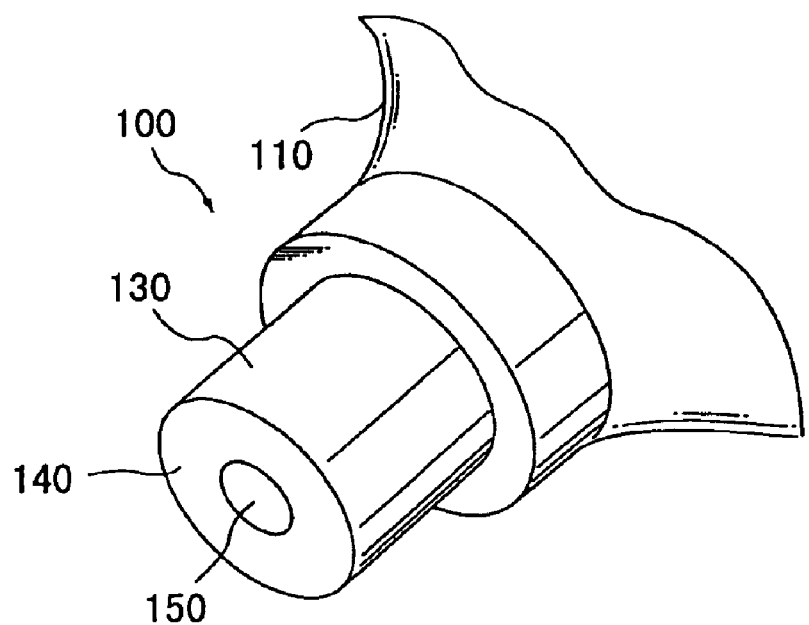
FIG. 11B is an enlarged partial perspective view showing a projection portion of the measuring apparatus shown in FIG. 11A.
Figure 12:
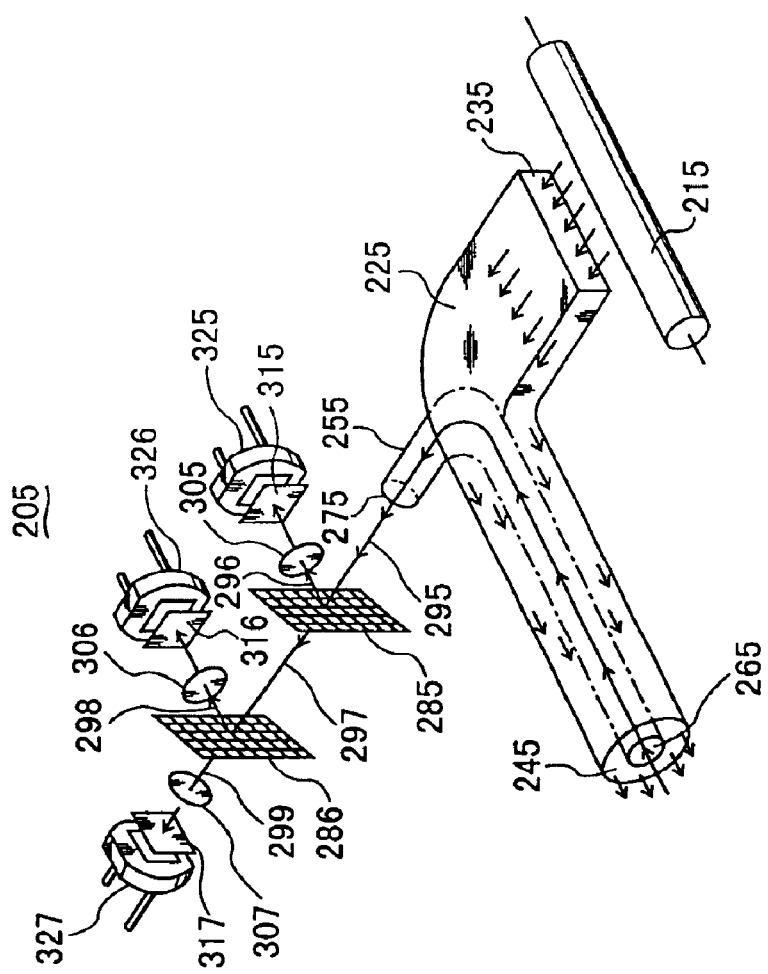
FIG. 12 is a perspective diagram showing an optical system of the measuring apparatus shown in FIG. 11A.

FIG. 11 is a perspective view showing a projection portion of the second embodiment, and FIG. 12 is a diagram showing an optical system of the second embodiment. This transcutaneous bilirubin concentration measuring apparatus 100 has a casing 110 of the size holdable in hand as shown in FIG. 11A. Inside the casing 110 are arranged an optical system and electric elements described later. Further, a display 120 for displaying a measurement result, i.e., a concentration of bilirubin pigmented in the subcutaneous fat is provided at the rear end of the upper surface of the casing 110.

A cylindrical projection 130 is projectably and retractably mountable on the leading end of the casing 110 as indicated by an arrow AR. This projection 130 is biased in such a direction as to project from the casing 110 (arrow direction AR) by a biasing means (not shown) such as a spring member. When a person who conducts a measurement presses the projection 130 against a part, such as a forehead, of a person to be measured, it is pushed into the casing 110 against a biasing force of the biasing means, thereby driving a xenon tube 215 (see FIG. 12) described later.

In the end face of the projection 13 are provided, as shown in FIG. 11B, an annular emerging port 140 through which luminous fluxes from the xenon tube 215 emerge out and a round incident port 150 which is defined inside the emerging port 140.

When the projection 130 is pushed in to drive the xenon tube 215, a white light from the xenon tube 215 emerges out through the emerging port 140 of the projection 130 shown in FIG. 11B and is incident on the skin of the person to be measured. Luminous fluxes diffused in the skin are incident on an optical system provided in the casing 110 via the incident port 150. Further, a power switch 110a and a reset switch 450 (see FIG. 13) are provided at a rear end of one side surface of the casing 110 in FIG. 11A and on a back surface thereof, respectively.

In FIG. 12, an optical system 205 is accommodated in the casing 110 shown in FIG. 11A. The optical system 205 has the xenon tube 215 (light emitting means) as a light source, and a light (white light) having a plurality of wavelengths is produced when the xenon tube 215 is driven.

One end 235 of an optical fiber 225 which acts as a light guiding means is opposed to the xenon tube 215. The luminous fluxes from the xenon tube 215 are introduced to an other end 245 thereof, and emerge therefrom through the emerging port 140 of the projection 130 (see FIG. 11).

These emergent luminous fluxes are incident on the skin of the person to be measured, and the luminous fluxes diffused in the skin as described later are incident on one end 265 of an optical fiber 255 via the incident port 150. The diffused luminous fluxes incident on the one end 265 of the optical fiber 255 are introduced to an other end 275 thereof and emerge therefrom. Luminous fluxes 295 emerged from the other end 275 are incident on a dichroic mirror 285 for reflecting luminous fluxes in the blue wavelength range, thereby splitting the luminous fluxes in two directions.

Luminous fluxes 296 reflected by the dichroic mirror 285 are gathered by a focusing lens 305 and received by a photoelectric conversion device 325 such as a photodiode via a blue filter 315. Luminous fluxes 297 having transmitted through the dichroic mirror 285 are incident on a dichroic mirror 286 through which the luminous fluxes in the red wavelength range transmit, thereby further being split in two directions.

Luminous fluxes 298 reflected by the dichroic mirror 286 are gathered by a focusing lens 306 and received by a photoelectric conversion device 326 such as a photodiode via a green filter 316. Further, luminous fluxes 299 having transmitted through the dichroic mirror 286 are gathered by a focusing lens 307 and received by a photoelectric conversion device 327 such as a photodiode via a red filter 317.

The dichroic mirror 285 constructs a first splitting means, and the dichroic mirror 286 constructs a second splitting means. Further, the photoelectric conversion device 325 constructs a first photoelectric conversion means; the photoelectric conversion device 326 constructs a second photoelectric conversion means; and the photoelectric conversion device 327 constructs a third photoelectric conversion means.

In the optical system 205 thus constructed, the luminous fluxes in the blue wavelength range (first wavelength range) are incident on the photoelectric conversion device 325, the luminous fluxes in the green wavelength range (second wavelength range) are incident on the photoelectric conversion device 326, and the luminous fluxes in the red wavelength range (third wavelength range) are incident on the photoelectric conversion device 327.

Figure 13:
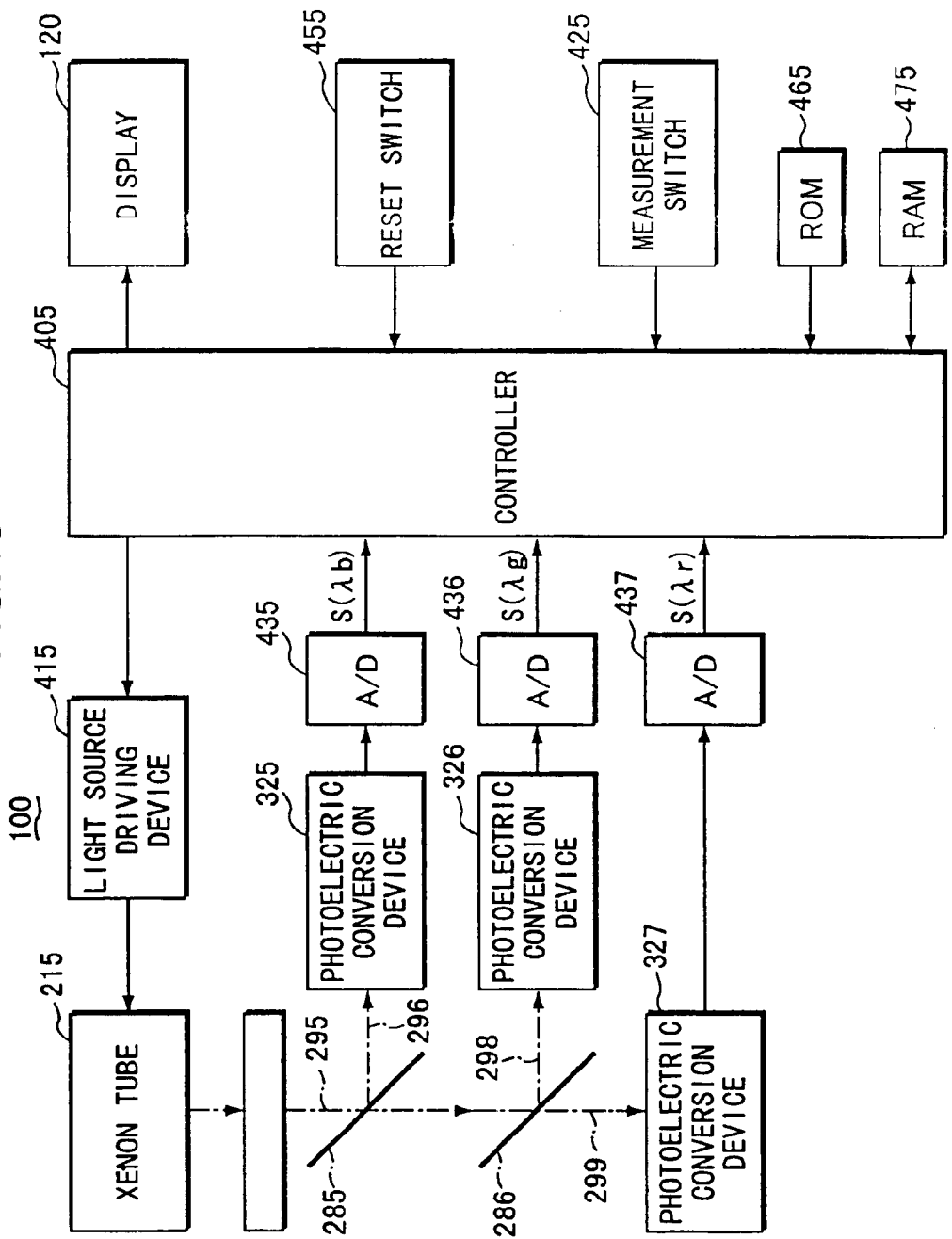
FIG. 13 is a block diagram showing an electric construction of the measuring apparatus shown in FIG. 11A.

FIG. 13 is a block diagram showing an electric construction of the measuring apparatus 100 shown in FIG. 11. This measuring apparatus 100 is provided with a controller 405 comprised of, e.g., a CPU, a light source driving device 415 for driving the xenon tube 215, a measurement switch 425 which is automatically turned on when the projection 130 (see FIG. 11) is pushed into the casing 110 against the biasing force of the biasing means as described above, A/D converters 435, 436, 437, a reset switch 45 for clearing the measurement result and bringing the apparatus into a state ready for a next measurement, a ROM 465 for storing a control program for the controller 405 and fixed data set in advance, and a RAM 475 for temporarily storing electric signal data and the like. The RAM (storage means) 475 has a backup power supply (not shown) lest the content in the memory should be erased. Instead of the RAM 47 having the backup power supply, a reloadable nonvolatile memory such as an EEPROM may be used as a storage means.

The controller 405 has a function as a light emission control means and is electrically connected with the light source driving device 415. As the projection 130 is pushed into the casing 11 against the biasing force of the biasing means as described above, the measurement switch 425 is automatically turned on and an emission command signal is accordingly sent from the controller 405 to the light source driving device 415, which in turn drives the xenon tube 215.

The photoelectric conversion devices 325, 326, 327 for receiving the luminous fluxes 296, 298, 299 split by the dichroic mirrors 285, 286, respectively are electrically connected with the controller 405 via the A/D converters 435, 436, 437, respectively. Electric signals $S(\lambda b)$, $S(\lambda g)$, $S(\lambda r)$ proportional to light reception amounts $I(\lambda b)$, $I(\lambda g)$, $I(\lambda r)$ are outputted from the photoelectric conversion device 325, 326, 327 to the controller 405.

The controller 405 also has a function as a concentration calculating means; calculates a bilirubin concentration in accordance with a measurement principle to be described later using the electric signals $S(\lambda b)$, $S(\lambda g)$, $S(\lambda r)$; and displays the calculation result on the display 120.

Next, a measurement principle of the second embodiment and the content of the calculation performed by the controller 405 are described. If $I_0(\lambda)$ denotes a light amount of the luminous fluxes incident on the skin, a light amount $I(\lambda)$ of the luminous fluxes incident on the measuring apparatus 100 through the incident port 150 is given by the following equations (31) and (32).

$$I(\lambda)=I_0(\lambda) \cdot F \cdot 10^{-K} \tag{31}$$

$$K=\epsilon_B(\lambda) \cdot C_B \cdot L + \epsilon_H(\lambda) \cdot C_H \cdot L \tag{32}$$

It should be noted that F denotes a light attenuation factor on the optical path other than bilirubin and melanin, $\epsilon_B(\lambda)$ denotes an absorption coefficient of bilirubin, $C_B$ denotes a bilirubin concentration, L denotes an effective optical path length of the optical path, $\epsilon_H(\lambda)$ denotes an absorption coefficient of melanin, and $C_H$ denotes a melanin concentration.

Here, if it is assumed that $E(\lambda b)$ denotes a measurement data obtained by the luminous fluxes in the blue wavelength range (wavelength $\lambda b$), the following equations (33), (34) can be obtained from equations (31), (32).

$$E(\lambda b)=A_b \cdot I(\lambda b)$$

$$=A_b \cdot I_0(\lambda) \cdot F \cdot 10^{-Kb} \tag{33}$$

$$Kb=\epsilon_B(\lambda b) \cdot C_B \cdot L + \epsilon_H(\lambda b) \cdot C_H \cdot L \tag{34}$$

Further, let it be assumed $E(\lambda g)$ denotes a measurement data obtained by the luminous, fluxes in the green wavelength range (wavelength $\lambda g$). Since bilirubin hardly absorbs the light in the green wavelength range, it is assumed that $\epsilon_B(\lambda g)=0$. Accordingly, the following equations (35), (36) can be obtained from equations (31), (32).

$$E(\lambda b) = A_g \cdot I(\lambda g)$$
$$= A_g \cdot I_0(\lambda g) \cdot F \cdot 10^{-Kg} \quad (35)$$
$$Kg = \epsilon_H(\lambda g) \cdot C_H \cdot L \quad (36).$$

Further, let it be assumed $E(\lambda r)$ denotes a measurement data by the luminous fluxes in the red wavelength range (wavelength $\lambda r$). Since bilirubin hardly absorbs the light in the red wavelength range, it is assumed that $\epsilon_B(\lambda r)=0$. Accordingly, the following equations (37), (38) can be obtained from equations (31), (32).

$$E(\lambda b) = A_r \cdot I(\lambda r)$$
$$= A_r \cdot I_0(\lambda r) \cdot F \cdot 10^{-Kr} \quad (37)$$
$$Kr = \epsilon_H(\lambda r) \cdot C_H \cdot L \quad (38).$$

It should be noted that $A_b$, $A_g$, $A_r$ denote constants corresponding to amplification factors. These constants $A_b$, $A_g$, $A_r$ are obtained prior to an actual measurement by performing a white calibration using a white diffusing plate such as an opaque plate having no wavelength dependency as a measurement sample. Since the measurement sample is the white diffusing plate having no wavelength dependency in the white calibration, $$F \cdot 10^{-Kb} = F \cdot 10^{-Kg} = F \cdot 10^{-Kr} = \text{constant}$$

in equations (33), (35), (37). Accordingly, if the constants $A_b$, $A_g$, $A_r$ are given such that $E(\lambda b)=E(\lambda g)=E(\lambda r)$, i.e., $A_b \cdot I(\lambda b) = A_g \cdot I(\lambda g) = A_r \cdot I(\lambda r)$ in the white calibration, $$A_b \cdot I_0(\lambda b) = A_g \cdot I_0(\lambda g) = A_r \cdot I_0(\lambda r) \quad (39).$$

The thus obtained constants $A_b$, $A_g$, $A_r$ are stored in the RAM 47.

An equation $\log\{E(\lambda g)/E(\lambda b)\}=Kb-Kg$ is obtained from equations (33), (35), (39). Following equation (40) is obtained from this equation and equations (34), (36):

$$\log\{E(\lambda g)/E(\lambda b)\}$$
$$= \epsilon_B(\lambda b) \cdot C_B \cdot L + \{\epsilon_H(\lambda b) - \epsilon_H(\lambda g)\} \cdot C_H \cdot L \quad (40).$$

Further, an equation $\log\{E(\lambda r)/E(\lambda g)\}=Kg-Kr$ is obtained from equations (35), (37), (39). Following equation (41) is obtained from this equation and equations (36), (38):

$$\log\{E(\lambda r)/E(\lambda g)\}$$
$$= \{\epsilon_B(\lambda g) - \epsilon_H(\lambda r)\} \cdot C_H \cdot L \quad (41).$$

By eliminating $C_H$ from equations (40), (41), the following equation (42) can be obtained:

$$\epsilon_B(\lambda b) \cdot C_B \cdot L$$
$$= \log\{E(\lambda g)/E(\lambda b)\}$$
$$- \{\epsilon_H(\lambda b) - \epsilon_H(\lambda g)\}/\{\epsilon_H(\lambda g) - \epsilon_H(\lambda r)\} \cdot \log\{E(\lambda r)/E(\lambda g)\} \quad (42).$$

In this way, the melanin concentration $C_H$ can be eliminated. If equation (42) is transposed while assuming z=the right side of equation (42), the following equation (43) can be obtained:

$$C_B = Z/\{\epsilon_B(\lambda b) \cdot L\} \quad (43).$$

Since $\epsilon_B(\lambda b)$, $\epsilon_H(\lambda b)$, $\epsilon_H(\lambda g)$, $\epsilon_H(\lambda r)$ are known in equation (42) or (43), they may be stored in the ROM 46.

Although it is difficult to accurately obtain the optical path length L, L is considered to be constantly a fixed value. Accordingly, a calibration is performed based on the measurement data obtained in accordance with equation (43) by the measuring apparatus 100 and an actual measurement value of the bilirubin concentration measured by an other method to determine the optical path length L. By storing this optical path length L in the ROM 46 in advance, the bilirubin concentration can be accurately calculated by eliminating the influence of the melanin concentration $C_H$.

The light reception amount $I(\lambda)$ is used in equations (31) to (43) in order to facilitate the description of the measurement principle. In the controller 405 of the inventive measuring apparatus 100, electric signals $S(\lambda b)$, $S(\lambda g)$, $S(\lambda r)$ proportional to the light reception amounts $I(\lambda b)$, $I(\lambda g)$, $I(\lambda r)$ are used instead of the light reception amounts $I(\lambda b)$, $I(\lambda g)$, $I(\lambda r)$ as described above. Measurement data $E(\lambda b)$, $E(\lambda g)$, $E(\lambda r)$ are calculated by multiplying the electric signals by the constants $A_b$, $A_g$, $A_r$ corresponding to the amplification factors stored in the RAM 47. The bilirubin concentration is calculated by obtaining logarithmic values of the aforementioned quotients:

$$\log\{E(\lambda g)/E_{1n}(\lambda b)\}$$
$$\log\{E(\lambda r)/E_{2n}(\lambda g)\}.$$

In this case, the electric signals $S(\lambda b)$, $S(\lambda g)$, $S(\lambda r)$ may be obtained a plurality of times, and the measurement data $E(\lambda b)$, $E(\lambda g)$, $E(\lambda r)$ may be calculated using average values of the electric signals $S(\lambda b)$, $S(\lambda g)$, $S(\lambda r)$.

The measuring operation of the measuring apparatus 100 thus constructed differs from that of the first embodiment in which the luminous fluxes in the two wavelength ranges are caused to propagate along the two optical paths in the skin, in that the luminous fluxes in the three wavelength ranges are caused to propagate along the same optical path in the skin. The measuring operation of the second embodiment is substantially the same as that of the first embodiment except in the content of the bilirubin concentration calculation due to the above difference.

Figure 14:
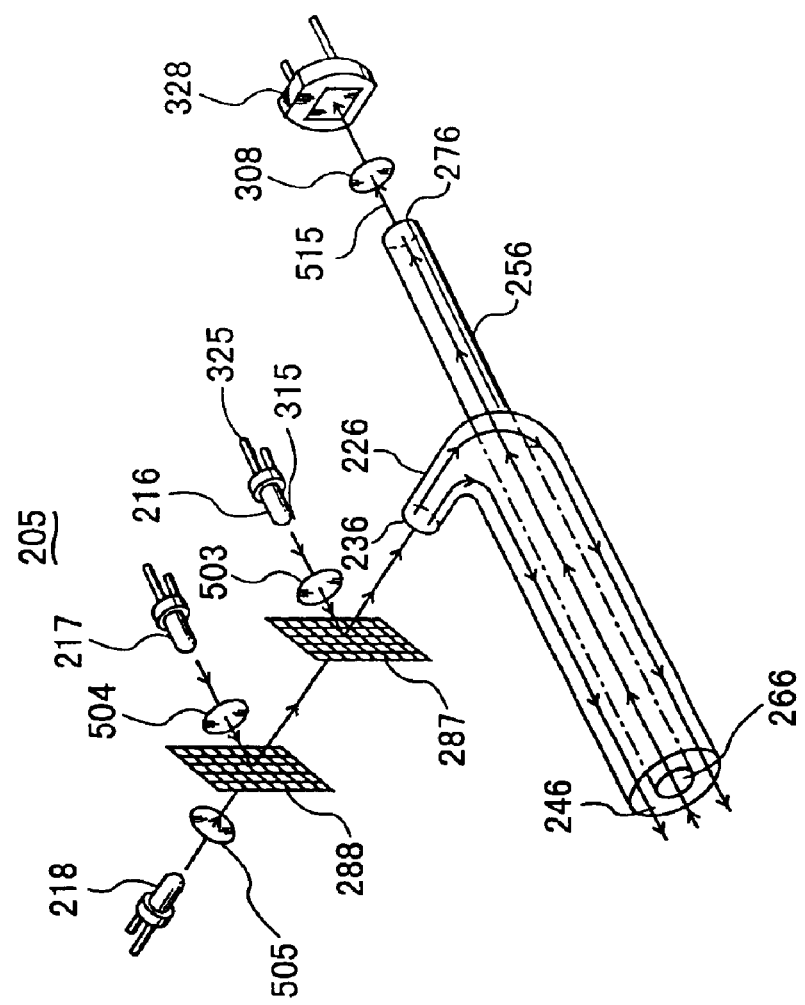
FIG. 14 is a modification of the optical system according to the second embodiment.

FIG. 14 is a diagram showing a modification of the optical system 205 of the second embodiment. It should be noted that no repetitive description is given by identifying the same elements as those of FIG. 12 by the same reference numerals.

Instead of the xenon tube 215, the optical system 205 of FIG. 14 has a blue LED 216 for emitting luminous fluxes in the blue wavelength range (first wavelength range), a green LED 217 an for emitting luminous fluxes in the green wavelength range (second wavelength range), and a red LED 218 for emitting luminous fluxes in the red wavelength range (third wavelength range) as light emitting means.

The luminous fluxes emitted from the blue LED 216 are collimated by a collimator lens 503, incident on and reflected by a dichroic mirror 287 for reflecting the light components in the blue wavelength range; the luminous fluxes emitted from the green LED 217 are collimated by a collimator lens 504, are incident on and reflected by a dichroic mirror 288 through which light components in the red wavelength range transmit; and the luminous fluxes emitted from the red LED 218 are collimated by a collimator lens 505, are incident on and reflected by the dichroic mirror 288 and are further incident on and transmit through the dichroic mirror 287.

One end 236 of an optical fiber 226 is opposed to the dichroic mirror 287, and the luminous fluxes having been reflected by and transmitted through the dichroic mirror 287 are incident on the one end 236 of the optical fiber 226 and introduced to an other end 246 thereof, and emerge therefrom through the emerging port 140 (see FIG. 11) of the projection 130.

The emerged luminous fluxes are incident on the skin of the person to be measured, and the luminous fluxes diffused in the skin are incident on one end 266 of an optical fiber 256 through the first incident port 150 (see FIG. 11) from the outer surface of the skin.

The diffused luminous fluxes incident on the one end 266 of the optical fiber 256 are introduced to an other end 276 thereof, and emerge therefrom. Luminous fluxes 515 emerged from the other end 276 are gathered by a focusing lens 308 and received by a photoelectric conversion device 328.

The blue LED 216 constructs a first light source; the green LED 217 constructs a second light source; and the red Led 218 constructs a third light source.

Figure 15:
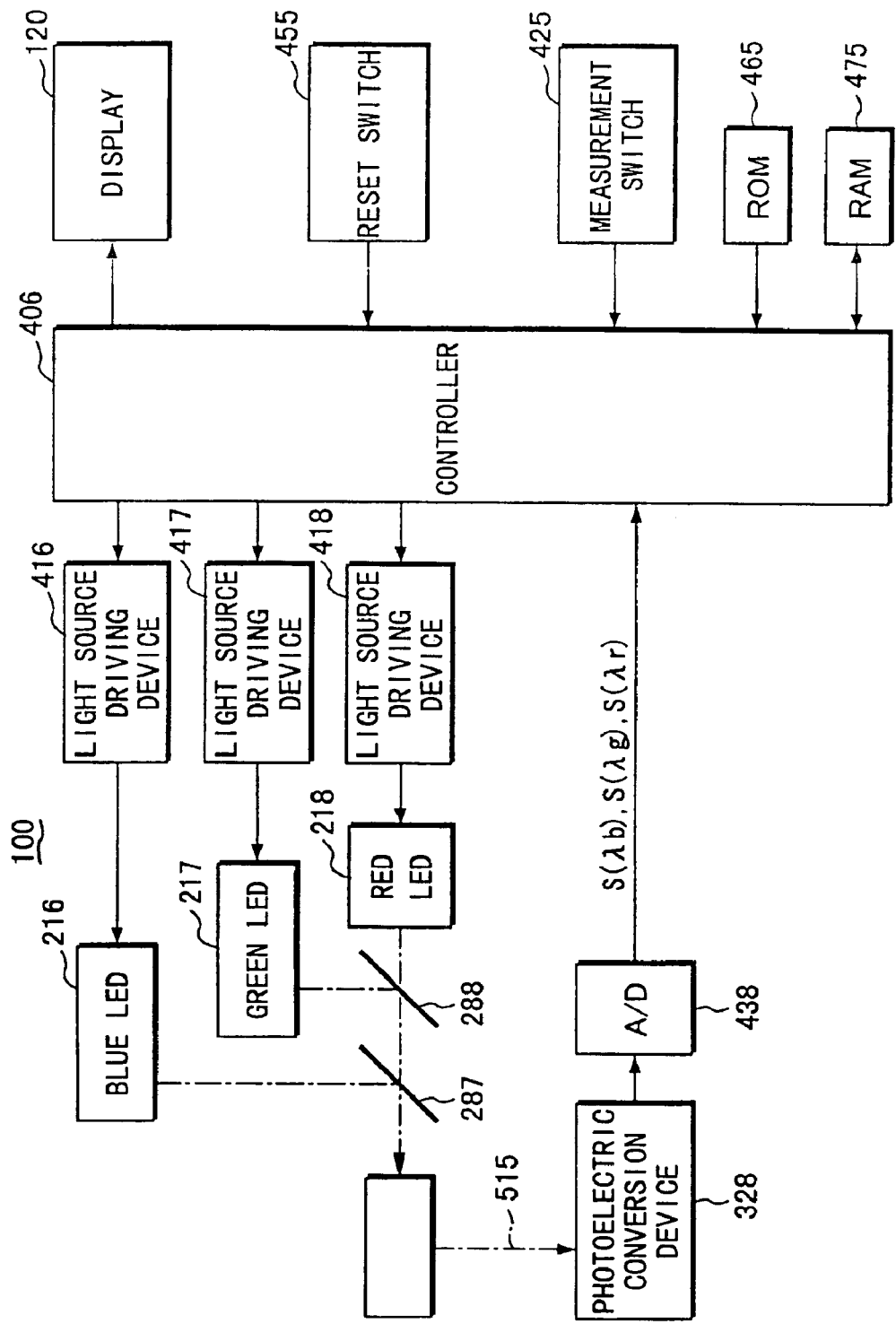
FIG. 15 is a block diagram showing an electric construction of a transcutaneous bilirubin concentration measuring apparatus having the optical system shown in FIG. 14.

FIG. 15 is a block diagram showing an electric construction of the bilirubin concentration measuring apparatus 100 having the optical system 205 shown in FIG. 14. It should be noted that the same elements as those of FIG. 13 are identified by the same reference numerals.

This measuring apparatus 100 is provided with a controller 406 comprised of, e.g., a CPU, a first light source driving device 416 for driving the blue LED 216, a second light source driving device 417 for driving the green LED 217, a third light source driving device 418 for driving the red LED 218, and an A/D converter 438.

The controller 406 has a function as a light emission control means and is electrically connected with the light source driving devices 416, 417, 418. As the projection 130 (see FIG. 11) is pushed into the casing 11 against the biasing force of the biasing means as described above, the measurement switch 425 is automatically turned on and emission command signals are individually sent from the controller 405 to the light source driving devices 416, 417, 418, which in turn drive the blue, green and red LEDs 216, 217, 218, respectively.

The photoelectric conversion device 328 for receiving the luminous fluxes 515 having transmitted through the optical fiber 256 (see FIG. 14) is electrically connected with the controller 406 via the A/D converter 438. Electric signal S(λb), S(λg), S(λr) proportional to light reception amounts I(λb), I(λg), I(λr) are outputted from the photoelectric conversion device 328 to the controller 406.

In similar to the controller 405, the controller 406 also has a function as a concentration calculating means, and calculates a bilirubin concentration in accordance with the aforementioned measurement principle using the electric signals S(λb), S(λg), S(λr) and displays the calculation result on the display 12.

Figure 8:
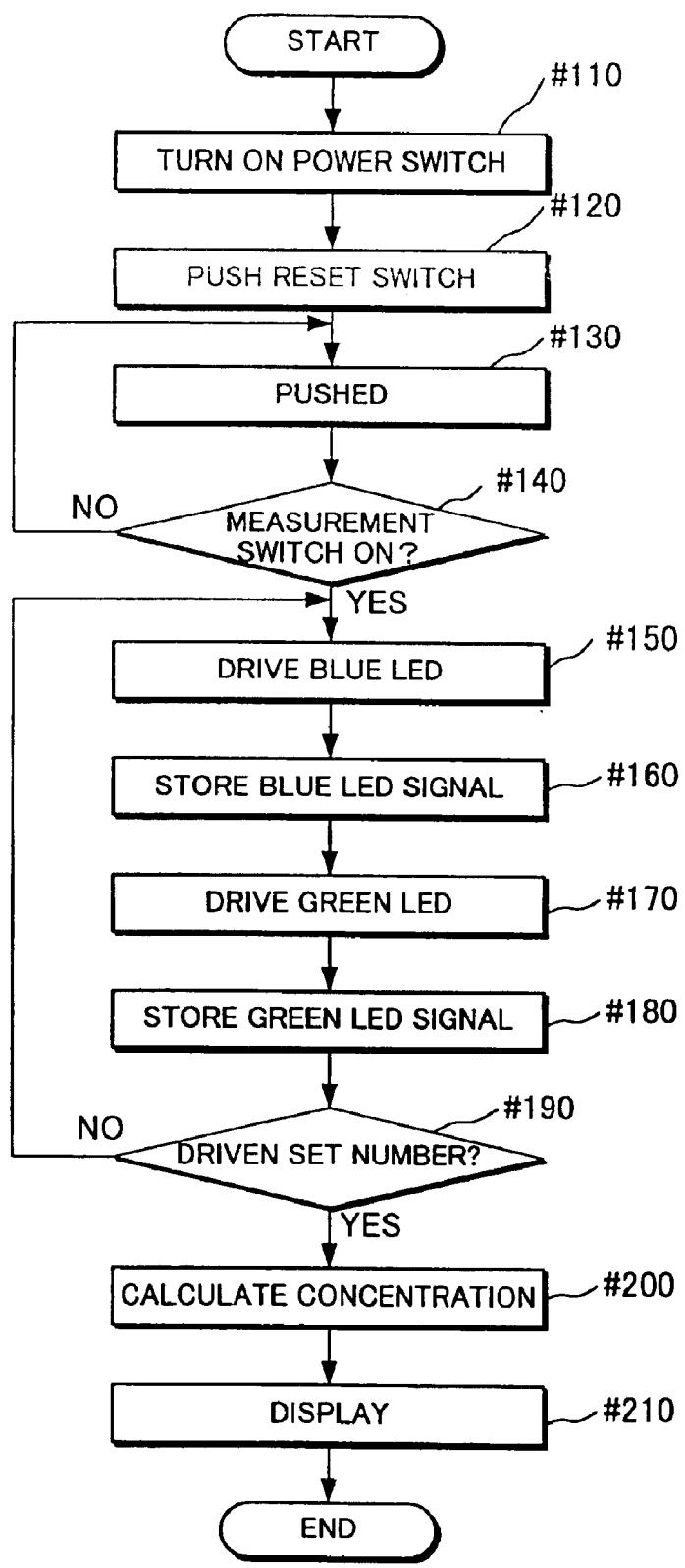
FIG. 8 is a flowchart showing a measuring operation of the measuring apparatus shown in FIG. 6.

A measuring operation of the measuring apparatus 100 having the optical system 205 of FIG. 14 constructed as above is basically the same as that of the flowchart of FIG. 8 except in that one more LED to be driven is provided and the content of the bilirubin concentration calculation differs.

According to this modification, as shown in FIG. 14, the blue LED 216 for emitting the luminous fluxes in the first wavelength range, the green LED 217 for emitting the luminous fluxes in the second wavelength range and the red LED 218 for emitting the luminous fluxes in the third wavelength range are provided and are individually driven. Thus, the number of large parts including the photoelectric conversion devices and the xenon tube can be reduced as compared with the case where the optical system 205 shown in FIG. 12 is used, thereby simplifying the construction of the optical system 205. Therefore, the casing 110 can be made even smaller.

Further, the respective LEDs 216, 217, 218, collimator lenses 503, 505, 505, and the dichroic mirrors 287, 288 are arranged on the same optic axis so that the luminous fluxes from the respective LEDs 216, 217, 218 are incident on the optical fiber 226 after being collimated into parallel luminous fluxes. Therefore, the emerging angle characteristics of the luminous fluxes of the respective colors at the emerging port 140 can be in agreement with each other, with the result that the measurement accuracy can be improved.

According to the invention, the control by the controller may be as described below in the first and second embodiments and the respective modifications. Specifically, electric signals from the photoelectric conversion devices 321, 361, 322, 362, 531, 532, 325, 326, 327, 328 are obtained while the light emitting means, e.g., the xenon tube 21 or 215 or the LEDs 211, 212, 216, 217, 218 are not driven, thereby generating reference data. Data obtained by subtracting the reference data from the electric signals obtained during the measurement by driving the light emitting means may be used for the calculation of the bilirubin concentration or data obtained by dividing the electric signals obtained during the measurement by the reference data may be used for the calculation of the bilirubin concentration. In this way, the influence of an external light can be eliminated, thereby improving the measurement accuracy.

Figure 16A:
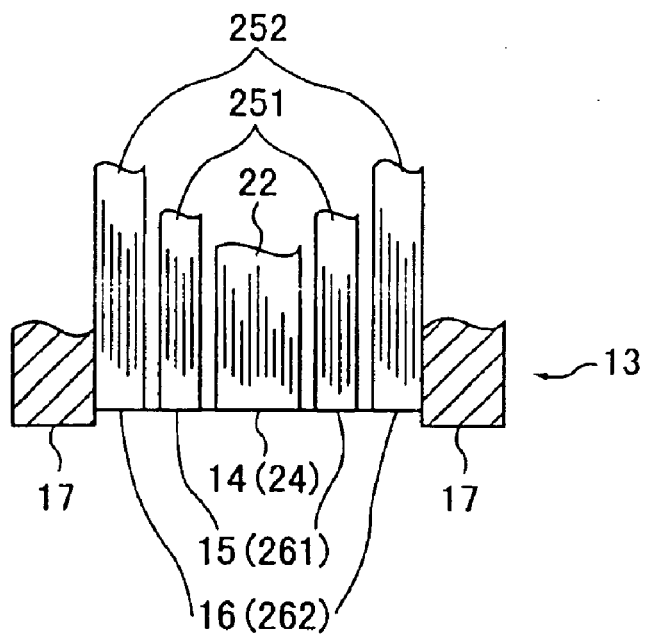
FIGS. 16A and 16B are sectional views showing modifications of the end face of the projection portion, respectively.
Figure 16B:
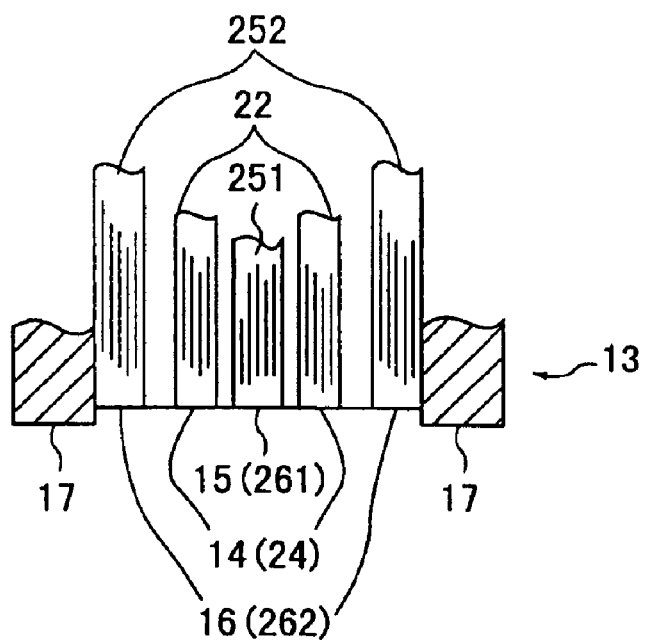

Further, the end face of the projection 13 shown in FIGS. 1 and 9 may be formed as shown in sections of FIGS. 16A and 16B. Specifically, the end faces of the emerging port 14, the first and second incident port 15, 16 and the light blocking portion 17 are located at different levels such that the end faces of the emerging port 14 and the first and second incident port 15, 16 are indented from that of the light blocking portion 17. Such an arrangement more satisfactorily prevents the intrusion of an external light when the projection 13 is pressed against the skin of the person to be measured, thereby further improving a measurement accuracy.

Figure 17A:
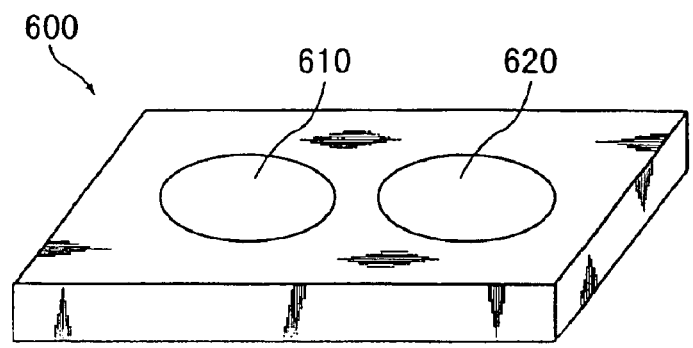
Figure 17B:
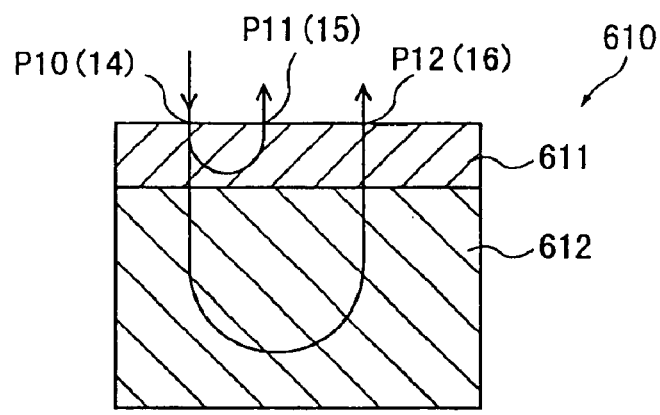
Figure 17C:
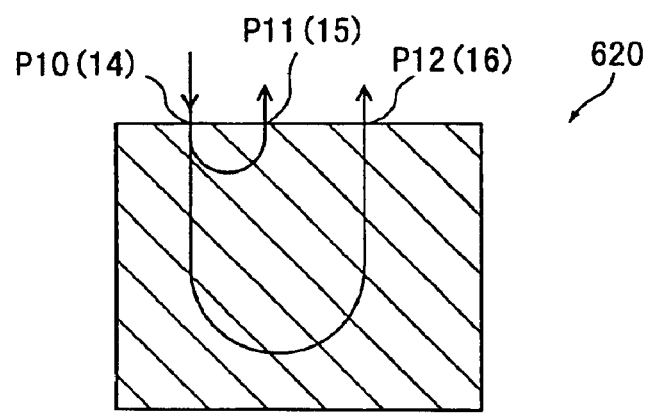
Figure 18:
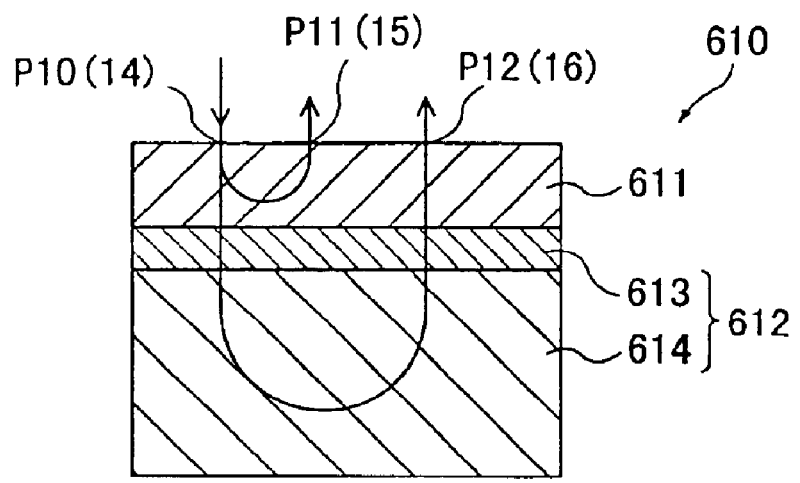
FIG. 18 is a sectional view showing a modification of the high concentration testing section of the checking plate shown in FIGS. 17A to 17C.

Next, a measurement data checking plate according to the invention is described with reference to FIGS. 17A to 17C. FIG. 17A is a perspective view showing an external configuration of the checking plate, FIG. 17B is a sectional view showing an internal configuration of a high concentration testing section and FIG. 17C is a sectional view showing an internal configuration of a low concentration testing section.

This measurement data checking plate is used as a measurement sample of the bilirubin concentration measuring apparatus 10 of the first embodiment to daily confirm an operation of the measuring apparatus as a checker for roughly checking whether or not the measurement data is satisfactory.

As shown in FIG. 17A, a measurement data checking plate 600 is provided with a high concentration checking section 610 and a low concentration checking section 620, which are respectively of the size that covers the emerging port 14 and the first and second incident ports 15, 16 of the projection 13 shown in FIG. 1.

The high concentration checking section 610 is comprised of a first diffusing layer 611 which is so provided on the top surface as to have a specified thickness and a second diffusing layer 612 formed below the first diffusing layer 611.

The first diffusing layer 611 is made of a material which has substantially the same absorption coefficient of the luminous fluxes in the blue wavelength range (first wavelength range) and absorption coefficient of the luminous fluxes in the green wavelength range (second wavelength range) and diffuses the incident luminous fluxes. This material may be, for example, an opaque plate (acrylic opaque plate, opal glass) or ground glass. The second diffusing layer 612 is made of a material whose absorption coefficient of the luminous fluxes in the blue wavelength range is larger than its absorption coefficient of the luminous fluxes in the green wavelength range and which diffuses the incident luminous fluxes. This material may be, for example, a yellow acrylic plate.

On the other hand, the low concentration checking section 620 is made of only the same or similar material as the first diffusing layer 611 of the high concentration checking section 610, such as an opaque plate or ground glass.

Next, an operation of the bilirubin concentration measuring apparatus 10 when the measurement sample is the measurement data checking plate 600 thus constructed is described.

When the light emitting means such as a xenon tube or an LED is driven by pushing the end face of the projection 13 shown in FIG. 1 against the high concentration checking section 610 of the measurement data checking plate 600, luminous fluxes are incident on point P10 corresponding to the emerging port 14; the luminous fluxes diffused in the first diffusing layer 611 emerge out from point P11 corresponding to the first incident port 15; and the luminous fluxes having reached the second diffusing layer 612 and diffused in a direction toward the top surface emerge out from point P12 corresponding to the second incident port 16 as diagrammatically shown in FIG. 17B.

Accordingly, the amount of incident light in the blue wavelength range and the amount of incident light in the green wavelength range are substantially at the same level in the luminous fluxes coming through the first incident port 15, whereas the amount of incident light in the blue wavelength range are more attenuated than the amount of incident light in the green wavelength range in the luminous fluxes coming through the second incident port 16.

Specifically, since equation (19) is expressed by $C_B = -J \cdot \log\{E_{2n}(\lambda g)/E_{2n}(\lambda b)\}$], a large numerical value is displayed as a bilirubin concentration on the display 12 (see FIG. 1).

Strictly speaking, it is not true that $\log\{E_{1n}(\lambda g)/E_{1n}(\lambda b)\}=0$ since the luminous fluxes coming through the first incident port 15 are also influenced by the second diffusing layer 612. However, its absolute value is negligibly small.

On the other hand, when the light emitting means is driven by pushing the end face of the projection 13 shown in FIG. 1 against the low concentration checking section 620 of the measurement data checking plate 600, luminous fluxes are incident on point P10 corresponding to the emerging port 14 and similarly diffused luminous fluxes emerge out from point P11 corresponding to the first incident port 15 and point P12 corresponding to the second incident port 16 as diagrammatically shown in FIG. 17C.

Since degrees of attenuation of the luminous fluxes in the blue and green wavelength ranges hardly differs between those coming out through the first incident port 15 and those coming out through the second incident port 16, a small numerical value is displayed as a bilirubin concentration on the display 12.

According to this embodiment, large and small numerical values can be displayed on the display 12 of the measuring apparatus 10 by using the measurement data checking plate 600 having the high and low concentration checking sections 610, 620 as the measurement sample. This enables the daily use of the measuring apparatus 10 as an easy checker.

Further, measurement values obtained when this measurement data checking plate 600 is used as the measurement sample may be stored in the RAM 47 or ROM 46 when the bilirubin concentration measuring apparatus 10 is manufactured. By suitably checking a variation of the measurement values for the checking plate 600 while the measuring apparatus 10 is being used, this checking plate 600 can be used as a standard calibration plate for checking the deterioration of the measuring apparatus 10 with time.

Further, since the high concentration checking section 610 is double-layered, its characteristics are degraded to a lesser degree with time, thereby improving productivity.

Preferably, the thickness of the first diffusing layer 611 is set at such a value as to provide characteristics similar to those of a new-born baby's skin based on the correlation with the characteristics of the new-born baby's skin.

The internal construction of the high concentration checking section 610 is not limited to the foregoing embodiment. For example, the second diffusing layer 612 may be comprised of a color filter layer 613 which is a thin plate formed adjacent to the first diffusing layer 611 and adapted to absorb luminous fluxes in the blue wavelength range, and a white diffusing layer 614 for diffusing the incident luminous fluxes.

The color filter layer 613 is made of a material whose absorption coefficient of the luminous fluxes in the blue wavelength range is larger than that of the luminous fluxes in the green wavelength range, for example, made of a yellow filter through which luminous fluxes in the yellow wavelength range transmit. The white diffusing layer 614 is made of the same material as the first diffusing layer 611, for example, made of an opaque plate (acrylic opaque plate or opal glass) or ground glass.

With this construction, the luminous fluxes having transmitted through the color filter layer 613 and diffused toward the top surface by the white diffusing layer 614 emerge out from point P12 corresponding to the second incident port 16. Accordingly, a large numerical value is displayed as a bilirubin concentration on the display 12 similar to the foregoing embodiment, with the result that the same effects as the foregoing embodiment can be obtained.

According to this modification, the second light diffusing layer 612 can be easily formed by the generally available color filter and opaque plate.

As described above, the luminous fluxes in the first and second wavelength ranges whose coefficients of absorption by bilirubin differ from each other are emitted and projected onto the skin of the person through the emerging port, and those diffused in the skin return to the measuring apparatus through the first incident port and the second incident port being differently distanced from the emerging port than the first incident port. Accordingly, the length of the second optical path along which the luminous fluxes returning through the second incident port propagate in the skin is longer than that of the first optical path along which the luminous fluxes returning through the first incident port propagate in the skin. By using the first and second electric signals corresponding to the first optical path and the third and fourth electric signals corresponding to the second optical path, a measurement error by melanin pigmented in the epidermis can be eliminated and the influences of the thicknesses of the epidermis and derma can be canceled out. Therefore, a measurement error caused by the degree of maturity of the skin can be eliminated, thereby improving the measurement accuracy of the bilirubin concentration.

The round emerging port is formed in the middle and the first and second annular incident ports are concentrically formed with the emerging port. Thus, a variation in the length of the optical paths of the luminous fluxes returning through the first and second incident ports can be reduced.

Alternatively, the round first incident port is formed in the middle, the annular emerging port is formed outside the first incident port, and the annular second incident port is formed outside the emerging port, i.e., the emerging port is formed between the first and second incident ports. Thus, the distance between the emerging port and the first incident port and the one between the emerging port and the second incident port can be set independently of each other, thereby increasing the degree of freedom in setting the length of the optical paths of the incident luminous fluxes.

Further, the white light containing luminous fluxes in the first and second wavelength ranges is emitted from the white light source; the diffused luminous fluxes incident through the first and second incident ports are split into the luminous fluxes in the first wavelength range and those in the second wavelength range by the first and second splitting means; the luminous fluxes in the first and second wavelength ranges having being incident through the first incident port, are received by the first and second photoelectric conversion devices, respectively; and the luminous fluxes in the first and second wavelength ranges having being incident through the second incident port are received by the third and fourth photoelectric conversion devices, respectively. Accordingly, the first to fourth electric signals can be suitably obtained only by driving the white light source once, thereby shortening the measurement time.

The diffused luminous fluxes incident through the first and second incident ports are guided to the first and second splitting means by the first and second light guiding means. This prevents the light reception amounts of the respective photoelectric conversion devices from being attenuated.

When the first light source for emitting luminous fluxes in the first wavelength ranges is driven, the luminous fluxes incident through the first and second incident ports are received by the first and second photoelectric conversion devices, respectively, to output the first and third electric signals. When the second light source for emitting luminous fluxes in the second wavelength ranges is driven, the luminous fluxes incident through the first and second incident ports are received by the first and second photoelectric conversion devices, respectively, to output the second and fourth electric signals. By individually providing the light sources for emitting the luminous fluxes in the first and second wavelength ranges, the splitting means for splitting the luminous fluxes needs not be provided. Therefore, the first to fourth electric signals can be suitably obtained by the simple construction comprised of a smaller number of parts.

In the above embodiment as well, the diffused luminous fluxes incident through the first and second incident ports are guided to the first and second splitting means by the first and second light guiding means. This prevents the light reception amounts of the respective photoelectric conversion devices from being attenuated.

Further, the first to fourth products obtained by multiplying the first to fourth electric signals by the first to fourth constants are obtained; the logarithmic number of the quotient obtained by dividing the second product by the first product is obtained; the logarithmic number of the quotient obtained by dividing the fourth product by the third product is obtained; and the bilirubin concentration is calculated using the difference between the two logarithmic numbers. In this way, the bilirubin concentration can be accurately calculated.

When the first and fourth electric signals obtained by driving the light emitting means with the white diffusing plate having no wavelength dependency opposed to the emerging port and the first and second incident ports are assumed as the first and fourth white electric signals, the first and second constants are set such that the product of the first white signal and the first constant and the product of the second white signal and the second constant are equal to each other, and the third and fourth constants are set such that the product of the third white signal and the third constant and the product of the fourth white signal and the fourth constant are equal to each other. In this way, the first to fourth constants can be suitably set, thereby enabling an accurate calculation of the bilirubin concentration.

Furthermore, the luminous fluxes in the first wavelength range which are absorbed by bilirubin, and those in the second and third wavelength ranges which are hardly absorbed by bilirubin are projected to the skin of the person through the emerging port; the luminous fluxes in the first, second and third wavelength ranges which were diffused in the skin are incident through the incident port and received; and the first, second and third electric signals having levels corresponding to the light reception amounts are outputted. Accordingly, a measurement error caused by melanin can be eliminated by obtaining a relationship independent of melanin concentration, thereby further improving the measurement accuracy of the bilirubin concentration.

Further, the white light containing luminous fluxes in the first, second and third wavelength ranges is emitted from the white light source; the diffused luminous fluxes incident through the incident port are split into the luminous fluxes in the first, second and third wavelength ranges by the first and second splitting means and received by the first, second and third photoelectric conversion devices, respectively. Accordingly, the first to third electric signals can be suitably obtained only by driving the white light source once, thereby shortening the measurement time.

When the first light source for emitting luminous fluxes in the first wavelength range is driven, the luminous fluxes incident through the incident port are received by the first photoelectric conversion device to output the first electric signal. When the second light source for emitting luminous fluxes in the second wavelength range is driven, the luminous fluxes incident through the incident port are received by the second photoelectric conversion device to output the second electric signal. When the third light source for emitting luminous fluxes in the third wavelength range is driven, the luminous fluxes incident through the incident port are received by the third photoelectric conversion device to output the third electric signal. By individually providing the light sources for emitting the luminous fluxes in the first, second and third wavelength ranges, the splitting means for splitting the luminous fluxes need not be provided. Therefore, the first to third electric signals can be suitably obtained by the simple construction comprised of a smaller number of parts.

Further, the first to third products obtained by multiplying the first to third electric signals by the first to third constants are obtained; the logarithmic number of the quotient obtained by dividing the second product by the first product is obtained; the logarithmic number of the quotient obtained by dividing the third product by the second product is obtained; and the bilirubin concentration is calculated using the two logarithmic numbers. In this way, the bilirubin concentration can be accurately calculated.

When the light emitting means is driven with the inventive measurement data checking plate opposed to the emerging port and the first and second incident ports, the luminous fluxes incident through the first incident port are those mainly diffused by the first light diffusing layer and the luminous fluxes incident through the second incident port also contain those diffused by the second light diffusing layer. Accordingly, a large numerical value can be obtained as the measurement result of the bilirubin concentration. Therefore, this checking plate can easily check the measuring apparatus.

Further, when the light emitting means is driven with the inventive measurement data checking plate opposed to the emerging port and the first and second incident ports, the luminous fluxes incident through the second incident port also contain those diffused by the white diffusing layer after transmitting through the color filter. Accordingly, a large numerical value can be obtained as the measurement result of the bilirubin concentration. Therefore, the measuring apparatus can be easily checked using the color filter.

As this invention may be embodied in several forms without departing from the spirit of essential characteristics thereof, the present embodiment is therefore illustrative and not restrictive, since the scope of the invention is defined by the appended claims rather than by the description preceding them, and all changes that fall within metes and bounds of the claims, or equivalence of such metes and bounds are therefore intended to embraced by the claims.

What is claimed is:

1. A bilirubin concentration measuring apparatus, comprising:
   (a) a light emitter for emitting a light which includes a first luminous flux falling in a first wavelength range and a second luminous flux falling in a second wavelength range, their bilirubin absorption coefficients differing from each other;
   (b) a light emerging port for projecting the light including the first and second luminous fluxes from the light emitter onto skin of a person for entering thereinto;
   (c) a first light incident port for allowing the first and second luminous fluxes having been diffused in tissues of the person to pass therethrough;
   (d) a second light incident port for allowing the first and second luminous fluxes having been diffused in tissues of the person to pass therethrough, the second light incident port being spaced away from the light emerging port a different distance than the first light incident port, so that optical path length of luminous fluxes which pass through the first light incident port and optical path length of luminous fluxes which pass through the second light incident port are different from each other;
   (e) a first electric signal generator for generating a first electric signal corresponding to an intensity of the first luminous flux passed through the first light incident port, and a second electric signal corresponding to an intensity of the second luminous flux passed through the first light incident port;
   (f) a second electric signal generator for generating a third electric signal corresponding to an intensity of the first luminous flux passed through the second light incident port, and a fourth electric signal corresponding to an intensity of the second luminous flux passed through the second light incident port; and
   (g) a calculator for calculating a bilirubin concentration based on the first to fourth electric signals se that includes a processor that cancels the influence of skin by using the luminous fluxes of the different optical path length.

2. The apparatus according to claim 1, wherein:
the light emerging port has the form of a circle and is disposed in a middle of a light incident plane;
the first light incident port has the form of a ring and is disposed on an outside of the light emerging port; and
the second light incident port has the form of a ring and is disposed on an outside of the first light incident port.

3. The apparatus according to claim 1, wherein:
the light emitter includes a white light source operable to emit white light containing the first and second luminous fluxes;
the first signal generator includes:
   a first light splitter for splitting the diffused luminous fluxes passed through the first light incident port into the first luminous flux and the second luminous flux;
   a first photoelectric conversion device for generating the first electric signal corresponding to the intensity of the first luminous flux split by the first light splitter; and
   a second photoelectric conversion device for generating the second electric signal corresponding to the intensity of the second luminous flux split by the first light splitter; and
the second signal generator includes:
   a second light splitter for splitting the diffused luminous fluxes passed through the
   second light incident port into the first luminous flux and the second luminous flux; a third photoelectric conversion device for generating the third electric signal corresponding to the intensity of the first luminous flux split by the second light splitter; and
   a fourth photoelectric conversion device for generating the fourth electric signal corresponding to the intensity of the second luminous flux split by the second light splitter.

4. The apparatus according to claim 3, further comprising:
a first light guiding member for guiding the diffused luminous fluxes passed through the first light incident port to the first light splitter; and
a second light guiding member for guiding the diffused luminous fluxes passed through the second light incident port to the second light splitter.

5. The apparatus according to claim 1, further comprising:
an emission controller for controlling the emission of the light emitter, wherein
the light emitter includes:
   a first light source operable to emit the first luminous flux; and
   a second light source operable to emit the second luminous flux;
the emission controller controls the first and second light sources to emit the first and second luminous fluxes separately;
the first electric signal generator includes a first photoelectric conversion device operable to individually generate the first and second electric signals based on the first and second luminous fluxes separately passed through the first light incident port; and
the second electric signal generator includes a second photoelectric conversion device operable to individually generate the third and fourth electric signals based on the first and second luminous fluxes separately passed through the second light incident port.

6. The apparatus according to claim 5, further comprising:
a first light guiding member for guiding the diffused luminous fluxes passed through the first light incident port to the first photoelectric conversion device; and
a second light guiding member for guiding the diffused luminous fluxes passed through the second light incident port to the second photoelectric conversion device.

7. The apparatus according to claim 5, wherein the first light source includes a blue light emitting diode, and the second light source includes a green light emitting diode or a red light emitting diode.

8. The apparatus according to claim 1, wherein the first luminous flux is absorbable by bilirubin, and the second luminous flux is hardly absorbable by bilirubin.

9. The apparatus according to claim 1, further comprising a memory for storing first to fourth constants corresponding to the first to fourth electric signals, respectively, wherein the calculator executes:
   calculation of first to fourth products by multiplying the first to fourth electric signals by the first to fourth constants;
   calculation of a first logarithmic number of a quotient obtained by division of the second product by the first product;
   calculation of a second logarithmic number of a quotient obtained by division of the fourth product by the third product; and
   calculation of a bilirubin concentration based on a difference between the calculated two logarithmic numbers.

10. The apparatus according to claim 9, further comprising:
    a constant calculator for calculating the first to fourth constants; and
    a storage controller for controlling storage of the calculated first to fourth constants in the memory, wherein the constant calculator calculates the first to fourth constants to assure the following relationships:
    1) a product of a first white electric signal and the first constant is equal to a product of a second white electric signal and the second constant; and
    2) a product of a third white electric signal and the third constant is equal to a product of a fourth white electric signal and the fourth constant,
    wherein the first to fourth white electric signals are first to second electric signals which are obtained under conditions where the first and second luminous fluxes are projected onto a white diffuser having no wavelength dependency, and the first and second luminous fluxes from the white diffuser are received after having passed through the first and second light incident ports.

11. The apparatus according to claim 1, further comprising:
    a projection operable to come into contact with skin of a person, the projection having a light-blocked potion and a non-light-blocked portion, wherein
    the light emerging port, and the first and second light incident ports are provided in the non-light-blocked portion of the projection.

12. A bilirubin concentration measuring apparatus, comprising:
    (a) a light emitter for emitting a light which includes a first luminous flux falling in a first wavelength range and a second luminous flux falling in a second wavelength range, their bilirubin absorption coefficients differing from each other;
    (b) a light emerging port for projecting the light including the first and second luminous fluxes from the light emitter onto skin of a person for entering thereinto;
    (c) a first light incident port for allowing the first and second luminous fluxes having been diffused in tissues of the person to pass therethrough;
    (d) a second light incident port for allowing the first and second luminous fluxes having been diffused in tissues of the person to pass therethrough, wherein the first light incident port and the second light incident port have forms of ring or circle having relative different radii so that the second light incident port being spaced away from the light emerging port a different distance than the first light incident port;
    (e) a first electric signal generator for generating a first electric signal corresponding to an intensity of the first luminous flux passed through the first light incident port, and a second electric signal corresponding to an intensity of the second luminous flux passed through the first light incident port;
    (f) a second electric signal generator for generating a third electric signal corresponding to an intensity of the first luminous flux passed through the second light incident port, and a fourth electric signal corresponding to an intensity of the second luminous flux passed through the second light incident port; and
    (g) a calculator for calculating a bilirubin concentration based on the first to fourth electric signals.

13. The apparatus according to claim 12, wherein:
    the light emitter includes a white light source operable to emit white light containing the first and second luminous fluxes;
    the first signal generator includes:
    a first light splitter for splitting the diffused luminous fluxes passed through the first light incident port into the first luminous flux and the second luminous flux;
    a first photoelectric conversion device for generating the first electric signal corresponding to the intensity of the first luminous flux split by the first light splitter; and
    a second photoelectric conversion device for generating the second electric signal corresponding to the intensity of the second luminous flux split by the first light splitter; and
    the second signal generator includes:
    a second light splitter for splitting the diffused luminous fluxes passed through the second light incident port into the first luminous flux and the second luminous flux;
    a third photoelectric conversion device for generating the third electric signal corresponding to the intensity of the first luminous flux split by the second light splitter; and
    a fourth photoelectric conversion device for generating the fourth electric signal corresponding to the intensity of the second luminous flux split by the second light splitter.

14. The apparatus according to claim 12, further comprising:
    an emission controller for controlling the emission of the light emitter, wherein
    the light emitter includes:
    a first light source operable to emit the first luminous flux; and
    a second light source operable to emit the second luminous flux;
    the emission controller controls the first and second light sources to emit the first and second luminous fluxes separately;
    the first electric signal generator includes a first photoelectric conversion device operable to individually generate the first and second electric signals based on the first and second luminous fluxes separately passed through the first light incident port; and the second electric signal generator includes a second photoelectric conversion device operable to individually generate the third and fourth electric signals based on the first and second luminous fluxes separately passed through the second light incident port.

15. The apparatus according to claim 12, wherein the first luminous flux is absorbable by bilirubin, and the second luminous flux is hardly absorbable by bilirubin.

16. The apparatus according to claim 12, further comprising a memory for storing first to fourth constants corresponding to the first to fourth electric signals, respectively, wherein the calculator executes:

calculation of first to fourth products by multiplying the first to fourth electric signals by the first to fourth constants;

calculation of a first logarithmic number of a quotient obtained by division of the second product by the first product;

calculation of a second logarithmic number of a quotient obtained by division of the fourth product by the third product; and calculation of a bilirubin concentration based on a difference between the calculated two logarithmic numbers.

17. The apparatus according to claim 12, further comprising:

a projection operable to come into contact with skin of a person, the projection having a lighted-blocked potion and a non-light-blocked portion, wherein the light emerging port, and the first and second light incident ports are provided in the non-light-blocked portion of the projection.

18. A bilirubin concentration measuring apparatus, comprising:

a light emitter for emitting a light which includes a first luminous flux falling in a first wavelength range and a second luminous flux falling in a second wavelength range, their bilirubin absorption coefficients differing from each other;

a light emerging port for projecting the first and second luminous fluxes onto skin of a person;

a first light incident port for allowing the first and second luminous fluxes having been diffused in the skin to pass therethrough;

a second light incident port for allowing the first and second luminous fluxes having been diffused in the skin to pass therethrough, the second light incident port being spaced away from the light emerging port a different distance than the first light incident port;

a first electric signal generator for generating a first electric signal corresponding to an intensity of the first luminous flux passed through the first light incident port, and a second electric signal corresponding to an intensity of the second luminous flux passed through the first light incident port;

a second electric signal generator for generating a third electric signal corresponding to an intensity of the first luminous flux passed through the second light incident port, and a fourth electric signal corresponding to an intensity of the second luminous flux passed through the second light incident port; and a calculator for calculating a bilirubin concentration based on the first to fourth electric signals wherein:

the first light incident port has the form of a circle and is disposed in a middle of a light incident plane;

the light emerging port has the form of a ring and is disposed on an outside of the first light incident port; and the second light incident port has the form of a ring and is disposed on an outside of the light emerging port.

* * * * *